US009669080B2

(12) United States Patent
Langlade Demoyen et al.

(10) Patent No.: US 9,669,080 B2
(45) Date of Patent: Jun. 6, 2017

(54) UNIVERSAL CANCER PEPTIDES DERIVED FROM TELOMERASE

(71) Applicants: INVECTYS, Paris (FR); Universite De Franche-Comte, Besancon (FR); Centre Hospitalier Regional Universitaire de Besancon, Besancon (FR)

(72) Inventors: Pierre Langlade Demoyen, Neuilly sur Seine (FR); Olivier Adotevi, Besancon (FR); Magalie Dosset, Besancon (FR)

(73) Assignees: INVECTYS, Paris (FR); Universite De Franche-Comte, Besancon (FR); Centre Hospitalier Regional Universitaire De Besancon, Besancon (FR)

( * ) Notice: Subject to any disclaimer, the term of this patent is extended or adjusted under 35 U.S.C. 154(b) by 0 days.

(21) Appl. No.: 14/385,534

(22) PCT Filed: Mar. 7, 2013

(86) PCT No.: PCT/EP2013/054592
§ 371 (c)(1),
(2) Date: Sep. 16, 2014

(87) PCT Pub. No.: WO2013/135553
PCT Pub. Date: Sep. 19, 2013

(65) Prior Publication Data
US 2015/0283219 A1 Oct. 8, 2015

Related U.S. Application Data

(60) Provisional application No. 61/621,075, filed on Apr. 6, 2012.

(30) Foreign Application Priority Data

Mar. 16, 2012 (EP) .................................... 12305319

(51) Int. Cl.
A61K 39/00 (2006.01)
C12N 9/12 (2006.01)
G01N 33/50 (2006.01)
G01N 33/574 (2006.01)

(52) U.S. Cl.
CPC .......... *A61K 39/0011* (2013.01); *A61K 39/00* (2013.01); *C12N 9/1276* (2013.01); *C12Y 207/07049* (2013.01); *G01N 33/505* (2013.01); *G01N 33/57492* (2013.01); *A61K 2039/53* (2013.01); *A61K 2039/55566* (2013.01); *A61K 2039/57* (2013.01); *A61K 2039/572* (2013.01); *A61K 2039/585* (2013.01); *G01N 2333/70514* (2013.01); *G01N 2333/9128* (2013.01)

(58) Field of Classification Search
None
See application file for complete search history.

(56) References Cited

U.S. PATENT DOCUMENTS

| 5,539,084 A * | 7/1996 | Geysen ................. C07K 1/047 530/332 |
| 5,840,839 A * | 11/1998 | Wang ................. C07K 14/4748 530/325 |
| 8,222,392 B2 | 7/2012 | Cech et al. |
| 2003/0143228 A1 | 7/2003 | Chen et al. |
| 2009/0269739 A1 | 10/2009 | Cech et al. |
| 2011/0318380 A1* | 12/2011 | Brix ................... A61K 39/0011 424/193.1 |

FOREIGN PATENT DOCUMENTS

| WO | 98/14593 | 4/1998 |
| WO | WO 03/038047 | 5/2003 |

OTHER PUBLICATIONS

Kiecker et al., Human Immunology, 2004, 65: 523-536.*
Reay et al., Journal of Immunology, 1994, 152:3946-3957.*
Klebanoff et al., Immunol. Rev. 2011, 239: 27-44.*
Adotevi, et al. "Immunogenic HLA-B *0702-Restricted Epitopes Derived from Human Telomerase Reverse Transcriptase that Elicit Antitumor Cytotoxic T-Cell Responses" Clin Cancer Res 2006, 12(10):3158-3167.
Adotevi, et al. "Targeting human telomerase reverse transcriptase with recombinant lentivector is highly effective to stimulate antitumor CD8 T-cell immunity in vivo" Blood 2010, 115(15):3025-3032.
Artandi, et al. "Telomeres and telomerase in cancer" Carcinogenesis 2010, 31(1):9-18.
Bevan "Helping the CD8+ T-cell response" Nature Reviews Immunology 2004, 4:595-602.
Hanahan, et al. "Hallmarks of Cancer: The Next Generation" Cell 2011, 144:646-674.
Martinez, et al. "Telomeric and extra-telomeric roles for telomerase and the telomere-binding proteins" nature Reviews Cancer 2011, 11:161-176.
Osen, et al. "Screening of Human Tumor Antigens for CD4+ T Cell Epitopes by Combination of HLA-Transgenic Mice, Recombinant Adenovirus and Antigen Peptide Libraries" PLoS One 2010, 5(11):e14137.
Scardino, et al. "HER-2/neu and hTERT Cryptic Epitopes as Novel Targets for Broad Spectrum Tumor Immunotherapy" The Journal of Immunology 2002, 168:5900-5906.
European Search Report and Opinion dated Sep. 24, 2012, which issued during prosecution of European Application No. 12305319.1, which corresponds to the present application.
Godet, et al. "Analysis of Spontaneous Tumor-Specific CD4 T-cell Immunity in Lung Cancer Using Promiscuous HLA-DR Telomerase-Derived Epitopes: Potential Synergistic Effect with Chemotherapy Response" Clinical Cancer Research: An Official Journal of the American Association for Cancer Research 2012, 18(10):2943-2953.

(Continued)

Primary Examiner — Hong Sang
(74) Attorney, Agent, or Firm — Troutman Sanders LLP

(57) ABSTRACT

The invention relates to a peptide of 15 to 20 amino acids deriving from TERT protein, which peptide is capable of (i) binding to HLA class II and (ii) stimulating a CD4 Th response. These universal cancer peptides are especially useful in anti-tumor immunotherapy and immunomonitoring.

Figure 1:
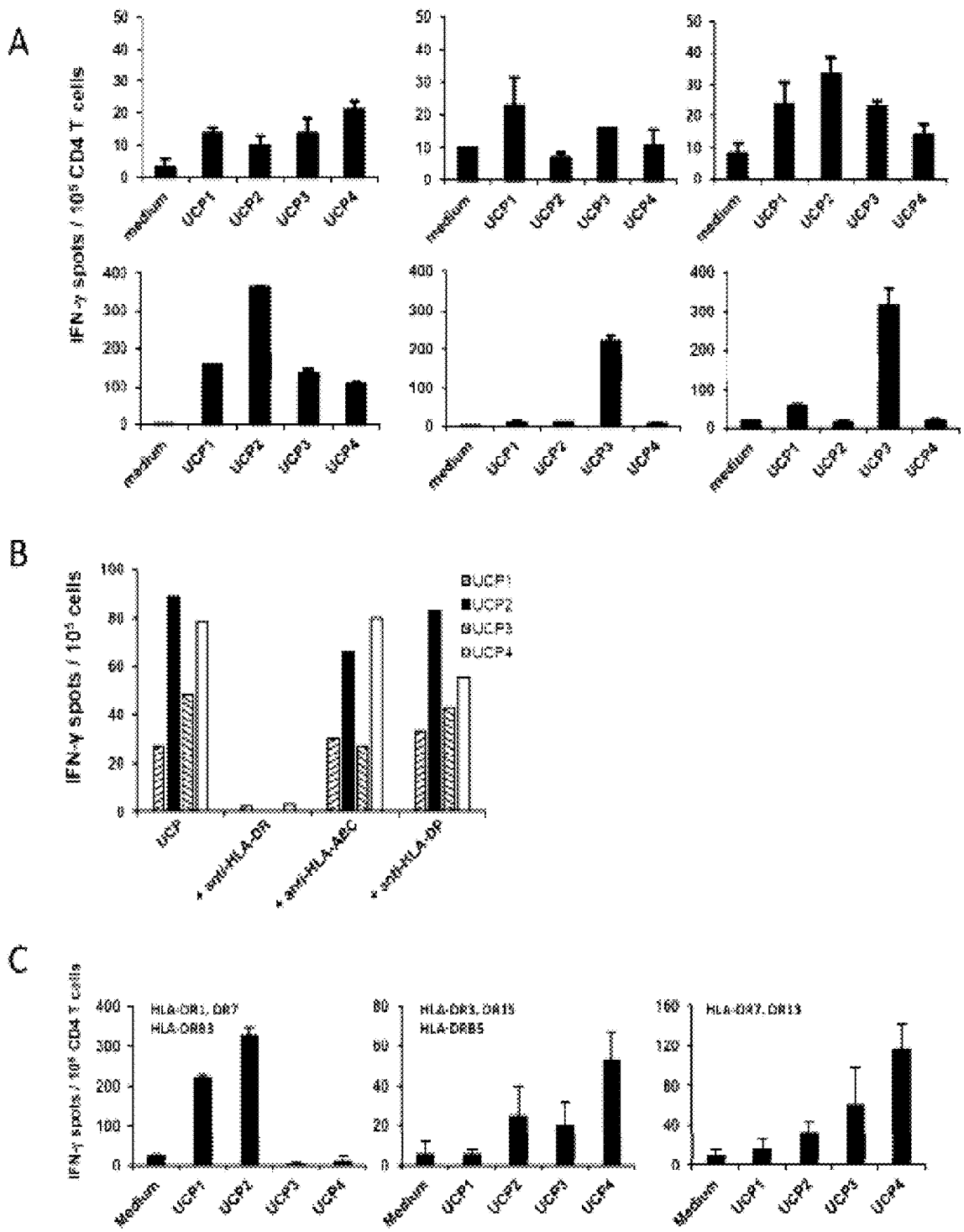

7 Claims, 17 Drawing Sheets
(3 of 17 Drawing Sheet(s) Filed in Color)

(56) References Cited

OTHER PUBLICATIONS

International Search Report and Written Opinion of the International Searching Authority dated Apr. 12, 2013, which issued during prosecution of International Application No. PCT/EP2013/054592 which corresponds to the present application.

Kyte, et al. "Telomerase Peptide Vaccination Combined with Temozolomide: A Clinical Trial in Stage IV Melanoma Patients" Clinical Cancer Research 2011, 17(13):4568-4580.

Schlapbach, et al. "Telomerase-specific GV1001 peptide vaccination fails to induce objective tumor response in patients with cutaneous T cell lymphoma" Journal of Dermatological Science 2011, 62(2):75-83.

Schroers, et al. "Human Telomerase Reverse Transcriptase-Specific T-Helper Responses Induced by Promiscuous Major Histocompatibility Complex Class II-Restricted Epitopes" Clinical Cancer Research: An Official Journal of the American Association for Cancer Research 2003, 9(13):4743-4755.

Schroers, et al. "Identification of HLA DR7-restricted Epitopes from Human Telomerase Reverse Transcriptase Recognized by CD4+ T-Helper Cells" Cancer Research, American Association for Cancer Research 2002, 62(9):2600-2605.

* cited by examiner

US 9,669,080 B2

UNIVERSAL CANCER PEPTIDES DERIVED FROM TELOMERASE

CROSS REFERENCE TO RELATED APPLICATIONS

This application is a U.S. National Phase Application under 35 U.S.C. §371 of International Patent Application PCT/EP2013/054592 filed Mar. 7, 2013, which claims priority to European Patent Application 12305319.1 filed Mar. 16, 2012 and claims the benefit of U.S. Provisional Application Ser. No. 61/621,075 filed Apr. 6, 2012. The International Application was published on Sep. 19, 2013, as International Publication No. WO 2013/135553A1 under PCT Article 21(2). The entire contents of these applications are hereby incorporated by reference.

The invention relates to epitopic peptides that derive from telomerase. These peptides are universal cancer peptides (UCPs) that bind to most commonly found MHC (Major Histocompatibility Complex) class II alleles. The peptides of the invention are capable of stimulating a CD4 Th response. These universal cancer peptides are especially useful in anti-tumor immunotherapy and immunomonitoring.

BACKGROUND OF THE INVENTION

The recent introduction of immunotherapy in clinical practice (Kantoff et al, Robert et al) emphasized the influence of immune responses on cancer prognosis and chemotherapy effectiveness. Among adaptive immune cells involved in antitumor responses, CD8 T cells (CTL) have been considered to be the main protagonists because they exhibit cytotoxic activity towards tumor cells expressing tumor associated antigens (TAAs). However, it is now clear that CD4 T helper 1 (Th1) lymphocytes also play a critical role in orchestrating the antitumor response. These cells, mainly characterized by INF-γ production, are critical for the induction and maintenance of CD8 T cells against tumors by providing help through multiple interactions (Shedlock et al). CD4 Th1 cells can also exert antitumor activity that is independent of CD8 T cells by recruiting and activating innate immune cell such as natural killers and macrophages (Kennedy et al, Perez-Diez et al). The IFN-γ secreted by CD4 Th1 cells also mediates direct antitumor or antiangiogenic effect (Street et al). A new dimension of CD4 Th1 cells role during cancer is also reported. It has been shown that CD4 T cells must pave the way for killer T-cell entry at tumor site (Bos et al) or infected mucosa (Nakanishi et al). Furthermore CD4 Th1 cells is required for the induction of cellular senescence and angiogenesis inhibition resulting in sustained tumor regression upon inactivation of the MYC or BCR-ABL oncogene in a mouse tumor model (Rakhra et al). In human, high density of tumor-infiltrating CD4 Th1 cells has been shown as good prognostic marker in colorectal cancer (Tosolini et al). Thus, stimulating CD4 Th1 cells is significant for improving antitumor responses. Despite recent progress indicating that pre-therapeutic immune parameters affect the efficacy of conventional chemotherapies (Fridman et al, Zitvogel et al), little is known about the relationship between tumor-specific CD4 Th1 immunity and efficacy of chemotherapy.

The CD4 Th cells recognize peptides of 15 to 20 amino acids presented by MHC class II molecules. MHC molecules in humans are normally referred to as HLA (Human Leucocyte Associated antigen) molecules. There are two principal classes of HLA molecules, HLA class I and HLA class II. HLA class I molecules primarily activate CD8+ cytotoxic T cells whereas HLA class II molecules primarily activate CD4 T cells. HLA class II molecules are encoded by 3 different subloci which are: HLA-DR, HLA-DQ and HLA-DP. However, CD4 T cell responses often described in cancer research are restricted to HLA class II molecule encoded by the HLA-DR sublocus. The identification of degenerate peptides of relevant TAAs able to bind to multiple HLA class II molecules may lead to improve cancer vaccine and to monitor CD4 T cell immunity. During the past years, different groups have focused on the identification of CD4 T cell epitopes from TAAs that could be used to improve anticancer immunotherapy. (Kobayashi et al, 2008, Campi et al, 2003, Kobayashi et al, 2000). However, the identification of HLA class II epitopes from TAAs is limited because of their important heterogeneicity. Indeed, the HLA class II locus is very polymorphic and have many variants, thus, finding peptides capable of binding multiple allelic variants of HLA-DR is a very hard work.

The telomerase protein has recently been the focus of attention for its supposed role in prevention of cellular ageing. Telomerase maintains telomere length in dividing cells and its over-expression is the predominant mechanism developed by malignant cells to escape telomere-dependent cell death (Martinez et al). Therefore, telomerase activity has been observed in all studied cancer forms, including stem cell-like tumor cells (Artandi et al) and is therefore a hallmark of cancer cells (Hanahan et al). Thus, telomerase seems to be a good prototype for universal TAAs. On this view, Telomerase-derived CD4 peptides could be very useful tools for developing immunotherapy in cancers.

International patent application WO 98/14593 discloses the amino acid sequence of human telomerase protein and also suggests the use of this protein and certain fragments thereof in active immunotherapy.

Schroers et al. have previously described TERT-derived promiscuous HLA-DR restricted peptides (Schroers et al, 2002 and 2003). However their role on cell-mediated tumor immunity was not completely addressed in preclinical models nor in a clinical setting. Recently, a cancer vaccine using a TERT-derived CD4 helper peptide was able to stimulate specific immune CD4 T immunity that could be related to an increased survival of cancer patients when combined with chemotherapy (Kyte et al, 2011; Schlapbach et al, 2011). Nevertheless, GV1001 vaccine also fails to induce specific immune responses and clinical benefit in other cancers (Scardino et al, 2002). Although this peptide is thought to congregate near CTL epitopes, the impact of GV1001-specific CD4 T cell help on antitumor CTL responses has not been investigated yet.

SUMMARY OF THE INVENTION

The invention is based on the discovery of new human TERT (telomerase reverse transcriptase) fragments capable of binding to a broad range of HLA class II molecules, and the use of these hTERT fragments for the treatment of diseases that require stimulating CD4 or CD8 T cell response, such as tumors.

The invention provides new universal HLA class II peptides derived from hTERT and referred to as universal cancer peptides (UCPs). These UCPs are capable of binding to most commonly found HLA-DR alleles, but also to HLA-DQ and HLA-DP alleles, and of stimulating a CD4 Th ("helper") response.

A first aspect of the invention is thus a peptide of 15 to 20 amino acids deriving from human telomerase reverse transcriptase, which peptide is capable of (i) binding to HLA class II and (ii) stimulating a CD4 Th response.

In a most preferred embodiment, the peptide comprises, or consists of, an amino acid sequence selected from the group consisting of:

```
KSVWSKLQSIGIRQH;            (SEQ ID NO: 1)

GTAFVQMPAHGLFPW;            (SEQ ID NO: 2)

SLCYSILKAKNAGMS;            (SEQ ID NO: 3)

PAAFRALVAQCLVCV;            (SEQ ID NO: 4)
``` peptide deriving from SEQ ID NO: 1, 2, 3 or 4 by any chemical modifications that improves their resistance to proteolysis;

and a substantially homologous peptide deriving from SEQ ID NO: 1, 2, 3 or 4 by substitutions of one or more amino acids, preferably a conservative substitution, or a substitution that improves immunogenicity of the peptide.

The invention also relates to a polypeptide of less than 160, preferably less than 120 amino acids, the sequence of which comprises at least two, preferably three, still preferably at least four different peptide sequences as previously defined, wherein said peptide sequences are optionally separated by an amino acid spacer. Preferably it is provided a polypeptide comprising SEQ ID NO:1, NO:2, NO:3, and NO:4, in any order.

The invention further relates to a polypeptide of less than 300, preferably less than 200 amino acids, comprising i) at least one peptide as described above, or comprising the polypeptide sequence of less than 160 or 120 amino acids as previously described, and ii) a CD8 epitopic peptide.

The invention further provides a nucleic acid encoding a peptide or a polypeptide as defined above.

The invention further provides a pharmaceutical composition comprising a peptide, a polypeptide or a nucleic acid as defined above, in association with a pharmaceutically acceptable excipient.

The invention also provides a pharmaceutical composition comprising a combination of the peptides defined above, preferably a combination of the four peptides of SEQ ID NO:1, 2, 3 and 4 or nucleic acids encoding said peptides.

In a particular embodiment, the composition is a vaccine composition further comprising an immunogenic antitumoral antigen or an immunogenic viral, bacterial or parasitic antigen.

The invention also refers to a pharmaceutical composition as defined above, for use in stimulating a CD4 or CD8 T cell response in a patient, or for use in treating a tumor or an infection in a patient, preferably a human patient.

In a particular embodiment, the tumor is a cancer, such as a cancer selected from the group consisting of chronic lymphocytic leukemia, chronic myeloid leukemia, multiple myeloma, malignant myeloma, Hodgkin's disease, melanoma, brain tumor such as glioblastoma, neuroblastoma and astrocytoytoma and carcinomas of the bladder, breast, cervix, colon, lung, pancreas, prostate, head and neck, or stomach. In a preferred embodiment, preferably wherein the tumor is a cancer induced by a virus, such a cervix cancer.

Another aspect of the invention is a conjugate comprising at least one peptide as defined above, bound to at least one HLA class II molecule, preferably a biotinylated HLA class II molecule.

Still another aspect of the invention is a conjugate as defined above, comprising at least four biotinylated HLA class II molecules to which at least four peptides as defined above are bound, wherein the at least four biotinylated HLA class II molecules are linked to each other through an avidine molecule that is optionally detectably labeled.

Such peptides or conjugates are further useful for in vivo, ex vivo and in vitro evaluation of a tumor-specific T cell response in a patient with a tumor.

The invention also encompasses an in vitro method for detecting or monitoring an anti-telomerase CD4 T cell response in a patient, which method comprises contacting a biological sample of the patient with a peptide, a polypeptide or a conjugate as defined above.

In a preferred embodiment, the patient is in need of a CD4 or CD8 T cell boosting therapy, preferably the patient has a tumor or is infected with a virus that infects telomerase-expressing cells.

In another preferred embodiment, the method described above is useful for determining or monitoring whether a patient is in need of a therapy or of an adjusted therapy, predicting the outcome of a patient, or for monitoring a response to a therapy.

SEQUENCE LISTING

The instant application contains a Sequence Listing which has been submitted in ASCII format via EFS-Web and is hereby incorporated by reference in its entirety. Said ASCII copy, created on Sep. 12, 2014, is named 246393.000002_SL.txt and is 1,284 bytes in size.

DETAILED DESCRIPTION OF THE INVENTION

The inventors have shown that the UCP-specific CD4 T cell response positively impacts overall survival in chemotherapy responding cancer patients. Indeed the inventors found that patients who are responding to chemotherapy benefit of natural antitumor immune response targeting UCPs. By contrast, when chemotherapy is ineffective, tumor lysis is low and consequently TERT antigen release is less available for the activation of the UCP-specific CD4 T response in vivo.

The inventors have now identified HLA class II peptides derived from hTERT, also called Universal Cancer Peptides (UCPs). These UCPs are surprisingly able to bind to the majority of human HLA-DR alleles, but also to HLA-DQ and HLA-DP alleles. They are endogenously processed and presented to CD4 T cells. Consequently, they stimulate CD4 Th cell responses, preferably CD4 Th1 cell response, against telomerase and have a helper effect on the cytotoxic activity of CD8 T cells.

These peptides are useful for boosting a CD4 or CD8 T cell response in any patient in need thereof, in particular in the therapy of cancers, especially as adjuvants, and in monitoring an anti-telomerase CD4 T cell response.

Peptide Characteristics:

The peptides of the invention derive from the telomerase protein.

The telomerase protein is a "tumor associated antigen" or "TAA". TAAs make tumor cells immunologically distinct from normal cells and provide diagnostic and therapeutic targets for human cancers. TAAs are very heterogeneous.

The peptides of the invention are capable of binding to HLA class II molecules and being presented to CD4 T cells. The peptides identified in the invention are referred as "UCPs" or "Universal cancer peptides", which means they are expressed in the majority of tumors. The UCPs of the invention are able to bind to a broad range of HLA class II alleles, more particularly to HLA-DR allele but also to HLA-DQ and HLA-DP alleles. In the present invention, the peptides are also referred as "HLA class II peptides".

The term "telomerase", as used herein, refers to an enzyme, a ribonucleoprotein polymerase, which maintains telomere ends. Telomerase is not expressed in most normal cells in the body. However, telomerase activity is detectable in cells which are in active division. Particularly, telomerase is over-expressed in malignant cells and telomerase activity has been observed in all studied cancer forms. In the present invention, telomerase is particularly referring to the subunit hTERT (human telomerase reverse transcriptase) of the telomerase complex. The subunit hTERT is the catalytic protein subunit of human telomerase. It is a protein of 127 kDa consisting of 1132 amino acids and made of different domains needed for its activity. hTERT present several advantages which are: i) its expression in most human cancers, ii) its oncogenic role essential for cell immortality and tumor growth which is preventing the antigenic loss tumor escape mechanism, iii) its constitutively high expression in cancer cells and cancer stem cells, and iv) its immunogenicity (Martinez et al, Hanahan et al).

The peptides of the invention are peptides of 15 to 20 amino acids deriving from hTERT. Preferably, the peptides of the invention are peptides of 15 to 17, preferably 15 amino acids deriving from hTERT.

The peptides as defined herein are capable of being presented as a complex with a plurality of HLA class II molecule on the surface of tumor cells or antigen presenting cells, thereby being useful in a majority of patients.

The peptides are capable of generating a CD4 Th cell response, preferably a Th1 cell response, directed against the telomerase protein.

The peptides are also capable of having a helper effect on the cytotoxic activity of CD8 T cells.

More particularly, four peptides have been identified by the inventors: UCP1 (p44), UCP2(p578), UCP3 (p916) and UCP4 (p1041). The amino acid sequences are presented in table 1 below.

TABLE 1

UCPs sequences

| Peptides | Sequences |
|---|---|
| UCP2 | KSVWSKLQSIGIRQH (SEQ ID NO: 1) |
| UCP3 | GTAFVQMPAHGLFPW (SEQ ID NO: 2) |
| UCP4 | SLCYSILKAKNAGMS (SEQ ID NO: 3) |
| UCP1 | PAAFRALVAQCLVCV (SEQ ID NO: 4) |

Other peptides of the invention are substantially homologous peptides deriving from SEQ ID NO: 1, 2, 3 or 4 by one, or more substitutions. Preferably the substitutions are conservative and/or improve the peptide immunogenicity.

The immunogenicity of the peptides can be improved by improving the binding affinity of the peptides to T cell receptors (TCR) present on CD4 T cells or/and by increasing the life time of the peptide-TCR complex.

Two amino acid sequences are "homologous", "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.). Preferably, these homologous peptides do not include two cysteine residues, so that cyclization is prevented.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties. Examples of conservative substitutions are set out in the Table 2 below:

TABLE 2

Conservative Substitutions I

| SIDE CHAIN CHARACTERISTIC | AMINO ACID |
|---|---|
| Non-polar | G A P I L V |
| Polar-uncharged | C S T M N Q |
| Polar-charged | D E K R |
| Aromatic | H F W Y |
| Other | N Q D E |

Alternatively, conservative amino acids can be grouped as described in Lehninger, 1975, as set out in Table 3, immediately below.

TABLE 3

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 4, immediately below.

TABLE 4

Conservative Substitutions III

| Original Residue | Exemplary Substitution |
|---|---|
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr (T) |
| Tyr (Y) | Trp (W), Phe (F), Thr (T), Ser (S) |
| Val (V) | Ile (I), Leu (L), Met (M), Phe (F), Ala (A) |

Peptide Preparation:

Peptides described herein can be synthesized using standard synthetic methods known to those skilled in the art., for example chemical synthesis or genetic recombination. In a preferred embodiment, peptides are obtained by stepwise condensation of amino acid residues, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl—Z (2-chlorobenzyloxycarbonyl), Br—Z (2-bromobenzyloyycarbonyl), Bzl (benzyl), Fmoc (9-fluorenylmcthoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Clz-Bzl (2,6-dichlorobenzyl) for the amino groups; $NO_2$ (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or trifluoromethane sulfonic acid for the Boc method, and with TFA for the Fmoc method.

Alternatively, the peptide may be synthesized using recombinant techniques. In this case, a nucleic acid and/or a genetic construct. comprising or consisting of a nucleotidic sequence encoding a peptide according to the invention, polynucleotides with nucleotidic sequences complementary to one of the above sequences and sequences hybridizing to said polynucleotides under stringent conditions.

The invention further relates to a genetic construct consisting of or comprising a polynucleotide sequence as defined herein, and regulatory sequences (such as a suitable promoter(s), enhancer(s), terminator(s), etc.) allowing the expression (e.g. transcription and translation) of a peptide according to the invention in a host cell.

Thus, in another aspect, the invention relates to a host or host cell that expresses (or that under suitable circumstances is capable of expressing) a peptide or polypeptide of the invention; and/or that contains a nucleic acid of the invention or genetic construct of the invention.

The method of producing the peptide may optionally comprise the steps of purifying said peptide, and/or chemically modifying said peptide.

Further Protection Against Proteolysis:

Peptides of the invention include peptides that derive from SEQ ID NO: 1, 2, 3 or 4 by any chemical modification that improves their resistance to proteolysis.

In particular, the N- and/or C-terminus of the peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH— peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH=CH— bond.

For instance the peptide may be modified by acetylation, acylation, amidation, crosslinking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

The peptides of the invention may be composed of amino acid(s) in D configuration, which render the peptides resistant to proteolysis. They may also be stabilized by intramolecular crosslinking, e.g. by modifying at least two amino acid residues with olefinic side chains, preferably C3-C8 alkenyl chains, preferably penten-2-yl chains, followed by chemical crosslinking of the chains, according to the so-called "staple" technology. For instance, amino acids at position i and i+4 to i+7 can be substituted by non-natural aminoacids that show reactive olefinic residues. All these proteolysis-resistant chemically-modified peptides are encompassed in the present invention.

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015).

Polypeptides

The invention also relates to a polypeptide of less than 160, preferably less than 120 amino acids comprising at least two, preferably three, still preferably at least four different peptide sequences as defined above.

The peptides may be in any order, from the N-terminus to the C-terminus of the polypeptide sequence.

Optionally, peptides are separated by an amino acid spacer. According to the invention, the spacer may generally comprise between 1 and 10 amino acids, preferably between 3 and 6 amino acids. The spacer sequence is selected so that it does not create new antigen sites with the contiguous peptides.

The invention further relates to a polypeptide of less than 300, preferably less than 200 amino acids comprising i) at least one peptide as defined above, and ii) a CD8 epitopic peptide.

Optionally, the polypeptide may comprise at least one amino acid spacer comprising between 1 and 10 amino acids, preferably between 3 and 6 amino acids.

The CD8 epitopic peptide is a peptide that is able to activate a CD8 T cell response against an antigen. Preferably, said CD8 epitope is able to activate a CD8 antitumoral response or a CD8 response against a viral, bacterial or parasitic antigen. Examples of tumoral antigens comprising said CD8 epitopic peptides include, but are not limited to: tyrosinase, alphafetoprotein, carcinoembryonic antigen (CEA), CA-125, MUC-1, epithelial tumor antigen, Melanoma-associated antigen, P1A, MART1/MELAN-1 and gp100/pMel17 as well as tyrosinase-related protein pg75 and MUM-1, HER2/neu, human papillomavirus proteins E6 and E7, GnT-V, beta-catenin, CDK4, p15, MAGE1, MAGE3, BAGE, GAGE, PSMA, TARP, STEAP, HTLV-1 Tax and WT1.

Examples of CD8 epitopic peptides include, but are not limited to: gp100.154, NA17-A.nt38, and MelanA/MART-1.27, CEA.571, Tyrosinase.368-N, p53.65, Her2/neu.369-377, gp100.209, gp100.476, Tyrosinase.368-D, MAGE-3.271, and Her2/neu.654, gp100.457, Melan-A/MART-1.32, Tyrosinase.I, p53.149, p53.264, and HPV E7.86. CD8 epitopic peptides from telomerase are pY988, pY572, p1, p4, p68, p277, p342, p351, p444, p464, p540, p865, p966, p1107 and p1123, (see US patent application US2009/175892A).

Nucleic Acids

The invention also relates to an isolated nucleic acid comprising or consisting of a nucleotide sequence encoding a peptide or polypeptide according to the invention.

The invention further relates to a genetic construct consisting of or comprising a polynucleotide sequence as defined herein, and regulatory sequences (such as a suitable promoter(s), enhancer(s), terminator(s), etc.) allowing the expression (e.g. transcription and translation) of a peptide according to the invention in a host cell.

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

In a particular embodiment, it is provided a nucleic acid coding for polypeptide of less than 160 or 120 amino acids as defined above.

Still another aspect of the invention includes a nucleic acid coding for a polypeptide of less than 300 or 200 amino acids comprising i) at least one peptide as defined above, and ii) a CD8 epitopic peptide, as defined above.

Conjugates

The peptide(s) of the invention can be bound to an HLA class II molecule to form a conjugate.

A conjugate comprises at least one peptide of the invention bound to at least one HLA class II molecule.

In a preferred embodiment, the HLA class II molecule is biotinylated.

Preferably, at least four peptides bound to four biotinylated HLA class II molecules are coupled with an avidin molecule and form a multimer, e.g. a tetramer or a pentamer. These conjugates efficiently bind a large amount of T cell receptors (TCR) present on CD4 T cells.

The CD4 T cells can easily be detected, for example by flow cytometry, if the avidin molecule is conjugated to a label. For example, the label can be a fluorochrome.

Thus, the conjugates described herein are very powerful tools to determine the level of CD4 T cells that are specific for the peptide(s) bound to the HLA class II molecule(s). In other words, the conjugates of the present invention allow the quantification of the TERT-specific CD4 T cell immune response in a patient.

Therefore, it is described a conjugate comprising at least four biotinylated HLA class II molecules to which at least four peptides according to the invention are bound, wherein the at least four biotinylated HLA class II molecules are linked to each other through an avidine molecule that is optionally detectably labeled. In a particular embodiment, the conjugate has four biotinylated HLA class II molecules to which four peptides according to the invention are bound, wherein the four biotinylated HLA class II molecules are linked to each other through an avidine molecule that is optionally detectably labeled.

Stimulation of a CD4 and/or a CD8 T Cell Response

The inventors have shown that the anti-telomerase CD4 Th1 immunity increases overall survival and progression free survival in patients with a tumor, especially in patients that responded to therapy, especially chemotherapy.

The inventors have further identified HLA class II peptides capable of triggering a TERT specific CD4 T cell response, and have shown that they significantly enhance the effects of an anti-tumoral vaccination.

The peptides of the invention (UCPs) are useful for stimulating (or boosting) a CD4 and/or a CD8 T cell response. The inventors have shown that UCPs vaccinations induced high avidity CD4 T cells that mostly produced IFN-γ as well as interleukin-2. UCP-specific CD4 T cells also induced activation and interleukin-12 production by dendritic cells. The inventors have further found that the presence of the UCPs of the invention in vaccine formulation drastically enhanced primary and memory anti-self tumor CD8 responses. This is explained by the "helper effect" of activated CD4 Th cells. In particular, tumor-reactive CD4+ T helper 1 T cells (Th1) produce several cytokines (such as IFN-γ, TNF-α and IL-2) essential for the induction of cell-mediated immunity against tumors (Kennedy et al, 2008). One widely accepted model demonstrates the ability of CD4+ T cells to recruit and/or activate dendritic cells (DCs) for efficient CD8+ T cell priming through the interaction of costimulatory receptors (Bennett et al, 1998; Smith et al, 2004).

The HLA class II peptides of the invention are useful therapeutic agents, in particular in immunotherapy of tumors in a patient, or for treating infections.

Preferably, the peptides of the invention may be used in combination, by administration of the four peptides of SEQ ID NO:1, SEQ ID NO:2, SEQ ID NO:3 and SEQ ID NO:4, either simultaneously or sequentially.

The term "patient", as used herein, refers to a mammal, preferably a human, including male, female, adult and children. The patient generally is a subject whose CD4 or CD8 T cells need stimulating. In a particular embodiment, the patient is affected with a tumor, especially a cancer. The tumor is preferably a cancer, such as a cancer selected from the group consisting of chronic lymphocytic leukemia, chronic myeloid leukemia, multiple myeloma, malignant myeloma, Hodgkin's disease, melanoma, brain tumor such as glioblastoma, neuroblastoma and astrocytoytoma and carcinomas of the bladder, breast, cervix, colon, lung, pancreas, prostate, head and neck cancer, or stomach cancer. Lung cancer, especially non-small cell lung cancer (NSCLC), is preferred.

In another preferred embodiment, the tumor is a cancer induced by a virus or an oncovirus. Such oncovirus include Human papilloma virus (HPV), Kaposi's sarcoma-associated herpesvirus (KSHV or HHV-8), Epstein-Barr virus (EBV or HHV-4), Merkel cell polyomavirus, or Human cytomegalovirus (CMV or HHV-5), as well as hepatitis C virus or human T-lymphotropic virus (HTLV-1).

The cancer may be at any stage of development, including the metastatic stage.

In another embodiment, the patient may be infected with a virus, a parasite or a bacteria. Examples of virus include papillomavirus, herpes simplex virus, hepatitis virus, adenovirus, myxovirus such as influenza, paramyxovirus, poxvirus such as Vaccinia, lentivirus such as HIV.

Preferably the patient to treat has undergone or is about to undergo a conventional therapy most preferably a first-line conventional therapy.

The UCP-based immunotherapy of the invention could be used in combination with conventional therapy The term "conventional therapy" means that the therapy is applied or, if not routinely applied, is appropriate and at least recommended by health authorities. In the case of cancer, the "conventional" treatment is selected by the physician depending on the specific cancer to treat. This more particularly includes chemotherapy, radiotherapy, hormonotherapy, immunotherapy, specific kinase inhibitor-based therapy and antibody-based therapy. Chemotherapy includes any compound such as any cytotoxic agent or cell death inducer, in particular a genotoxic agent, alone or in combination. Radiotherapy includes any irradiation treatment selected for example from X-rays, gamma irradiation and/or UVC irradiation. Hormonotherapy, i.e., a therapy leading to apoptosis or Fas ligands or soluble/membrane bound TRAIL or soluble/membrane bound TNF alpha (TNFα), includes a compound such as an antiaromatase for example. Immunotherapy includes a cytokine or an interferon, or a vaccine. Specific kinase inhibitor-based therapy includes a compound selected for example from a tyrosine kinase inhibitor, serine kinase inhibitor and a threonine kinase inhibitor.

In a preferred embodiment, the peptide(s) or the nucleic acid encoding said peptide(s) are an adjuvant therapy, e.g. they are used in combination with a chemotherapy or an anti-tumoral vaccination.

The peptides of the invention, or nucleic acids encoding the peptides, can be used for the treatment of a tumor or an infection in a patient, by generating a CD4 Th cell response, preferably a CD4 Th1 cell response, against telomerase and by having a helper effect on CD8 T cells antitumoral activity. Side-effects of such treatment are reduced. Indeed most healthy cells in the body of an organism do not express the telomerase protein, whereas cancerous cells over-express the telomerase protein. Therefore, healthy cells remain unaffected upon treatment with the peptide(s) of the invention.

The efficacy of the peptides of the invention is increased by the helper effect on CD8 T cells. The peptides of the invention, by stimulating CD4 T cells, have a helper effect on CD8 T cells antitumoral activity. Indeed, CD4 T cells are critical for the induction and maintenance of CD8 T cells against tumoral cells. The peptides described herein can congregate near CD8 epitopes and promote cytotoxic activity of CD8 T cells.

As used herein, the term "treatment" or "therapy" includes curative and/or preventive treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder. Preventive treatment refers to any of: halting the onset, reducing the risk of development, reducing the incidence, delaying the onset, reducing the development, as well as increasing the time to onset of symptoms of a particular disorder. Prevention is particularly interesting to prevent preneoplastic lesions.

Thus, the invention also relates to a vaccine useful in preventing a tumor.

It is thus described a method for treating a tumor or an infection in a patient in need thereof, which method comprises administering said patient with one or more peptide (s), or a nucleic acid encoding said peptide(s).

The inventors have shown that some patients with a cancer do not show or have a reduced CD4 Th1 cells response against telomerase. The survival in patients who do not spontaneously develop a telomerase-specific CD4 Th1 cell response is inferior to those who do develop such spontaneous telomerase-specific CD4 Th1 cell response.

Thus, the invention is more particularly directed to peptides as described herein (or nucleic acids that encode said peptides) particularly useful when the patient is not spontaneously capable of producing an anti-telomerase immune response. In these groups of patients, the treatment of the invention triggers a telomerase-specific CD4, especially CD4 Th1, T cell response that improves overall survival of the patients. In these patients, the peptides of the invention (or nucleic acids that encode the peptides) are preferably used as an adjuvant therapy, i.e. preferably in combination with a chemotherapeutic or an antitumoral vaccine. The treatment of the invention is also useful in patients who spontaneously develop a telomerase-specific CD4, especially CD4 Th1, T cell response, by boosting said response and further improving overall survival of the patients. In those patients, the peptides of the invention (or nucleic acids that encode the peptides) are be used either alone or as an adjuvant therapy, i.e. preferably in combination with a chemotherapeutic or an antitumoral vaccine Pharmaceutical Compositions It is provided pharmaceutical compositions comprising a peptide or a polypeptide as defined herein, or a nucleic acid encoding such peptide or polypeptide, in association with a pharmaceutically acceptable excipient. Preferably the composition may comprise a combination of peptides, still preferably a combination of the four peptides of SEQ ID NO:1, SEQ ID NO:2, SEQ ID NO:3 and SEQ ID NO:4.

The therapeutic agent, such as the peptide, the polypeptide, or the nucleic acid, is formulated in association with a pharmaceutically acceptable carrier.

The pharmaceutical composition may also include any other active principle, such as in particular an anti-cancer agents, e.g. conventional cytotoxic chemotherapies with inhibitors of DNA replication such as DNA binding agents in particular alkylating or intercalating drugs, antimetabolite agents such as DNA polymerase inhibitors, or topoisomerase I or II inhibitors, with anti-mitogenic agents such as alkaloids or with cancer growth blocking agents such as tyrosinase inhibitor or monoclonal antibodies, In a particular embodiment, the peptide, the polypeptide or the nucleic acid of the invention, is used in a vaccine composition. The vaccine composition preferably comprises a further immunogenic tumor antigen, preferably a peptide tumor antigen, which tumor antigen differentially targets an immune response against cancer cells.

Examples of such tumor antigens are described above.

The vaccine composition preferably comprises a further immunogenic viral, bacterial or parasitic antigen, preferably a peptide viral, bacterial or parasitic antigen, which viral, bacterial or parasitic antigen differentially targets an immune response against an infection.

In another embodiment, the peptides or polypeptides of the invention are combined with CD8 epitopic peptides deriving from telomerase.

The peptides or the polypeptides of the invention (or nucleic acid that encode said peptide(s) or polypeptide(s)) may be administered by any convenient route including intravenous, oral, transdermal, subcutaneous, mucosal, intramuscular, intrapulmonary, intranasal, parenteral, rectal, vaginal and topical. Intranasal route is of particular interest.

Advantageously, intra-tumoral administration is also contemplated.

In a preferred embodiment, the therapeutic agent, preferably the nucleic acid, may be administered by electroporation, in muscles or through the skin.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

Adjuvants may be added, such as aluminium salts, such as aluminium hydroxide, aluminium phosphate, aluminium sulphate, surface active substances such as lysolecithin; pluronic polyols; polyanions; peptides; and oil emulsions, Freund's complete and incomplete adjuvants, MPL-TDM adjuvant (monophosphoryl Lipid A, synthetic trehalose dicorynomycoiate), tyrosine, alumina, saponin adjuvants such as Stimulon™, cytokines, to enhance the efficacy of the composition.

Preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product.

The peptides of the invention (or the nucleic acids encoding said peptides) may be administered as a combination of peptides (or nucleic acids encoding said peptides).

The dosing is selected by the skilled person so that a stimulation of CD4 T cell response is achieved, and depends on the route of administration and the dosage form that is used. Total daily dose of the peptide administered to a subject in single or divided doses may be in amounts, for example, of from about 1 µg to 10 mg daily, preferably from 100 µg to 5 mg daily. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Diagnostic, Prognostic and Immunomonitoring

The peptide, the polypeptide or the conjugate of the invention may be used for the evaluation of a telomerase-specific CD4 T cell response, in particular in a patient with a tumor or an infection, in a biological sample.

The term "biological sample" refers to any biological sample originating from a patient. Examples of samples include biological fluids and tissue biopsies. Preferably, the sample may be blood, serum, saliva, urine or sperm. More preferably, the biological sample is a blood sample.

The peptide, the polypeptide or the conjugate of the invention may especially be used for the evaluation of a tumor-specific CD4 T cell response in a patient with a tumor, either before, during or after a conventional therapy.

According to the invention, the UCPs can be used for detecting or monitoring an anti-telomerase CD4 T cell response in a patient. Particularly, the peptides of the invention allow the monitoring of the anti-telomerase CD4 T cell response after a vaccination.

In one aspect of the invention, the patient is in need of a CD4 or CD8 T cell boosting therapy.

According to a particular aspect of the invention, this UCP-specific immunity response is quantified before, during and after a conventional therapy, to determine if the patient is in need of an adjuvant therapy, such as the peptides described in the present invention, and to adapt or adjust said adjuvant therapy.

This is particularly useful to determine if the patient is "responder" or likely to respond to the conventional treatment, especially chemotherapy.

Within the context of this invention, a patient is considered "responder" if at least one of his symptoms is expected to be alleviated, or the development of the disease is stopped, or slowed down. Complete responders, partial responders, or stable patients with cancers can be defined according to the RECIST criteria (Eisenhauer et al, European Journal of Cancer, 2009, 45:228-247). In solid tumors, the RECIST criteria are an international standard based on the presence of at least one measurable lesion. "Complete response" means disappearance of all target lesions; "partial response" means 30% decrease in the sum of the longest diameter of target lesions, "progressive disease" means 20% increase in the sum of the longest diameter of target lesions, "stable disease" means changes that do not meet above criteria. Thus, the peptides or the conjugates of the invention can be used to determine if a patient having a tumor is in need of an adjuvant therapy, that may preferably be a pharmaceutical composition comprising said peptide(s) or a nucleic acid encoding said peptide(s), or whether the dosage regimen of such therapy or composition should be adjusted (i.e. increased, continued, decreased, or stopped).

The peptides of the invention allow determining the anti-telomerase CD4 Th cell response after a treatment or a vaccination, especially an anti-tumoral therapy that involves lysis of tumor cells or anti-infectious therapy that involves lysis of infected telomerase-expressing cells. Such therapies may rely on the peptides or polypeptides of the invention, but are not limited to said peptides or polypeptides.

The below embodiments are exemplified based on the peptides or polypeptides of the invention, but could similarly be applied to other therapies, as long as the peptides, polypeptides or conjugates of the invention are used to detect an anti-telomerase T cell response.

In a first particular embodiment, it is provided a method for determining or monitoring whether a patient having a tumor or an infection is in need of an adjuvant therapy or of an adjusted adjuvant therapy, which method comprises stimulating Peripheral Blood Mononuclear Cells (PBMC) obtained from a biological sample of the patient with a peptide, a polypeptide, or a conjugate as defined herein, and determining the level of CD4 Th cells that are specific for the peptide or the conjugate, wherein a level of CD4 Th cells inferior to a control value is indicative of a patient in need of an adjuvant therapy or of an adjusted adjuvant therapy.

More particularly, it is provided an in vitro method for determining whether a patient having a tumor or an infection is in need of an adjuvant therapy, that is preferably a pharmaceutical composition comprising the peptide(s) of the invention or a nucleic acid encoding said peptide(s), which method comprises stimulating Peripheral Blood Mononuclear Cells (PBMC) obtained from a biological sample of the patient with a peptide, polypeptide, or a conjugate as defined herein, and determining the level of CD4 Th cells that are specific for the peptide or the conjugate, wherein a level of CD4 Th cells inferior to a control value is indicative of a patient in need of an adjuvant therapy.

According to this aspect of the invention, the "control value" may be established from the level of anti-TERT CD4 Th cells in a biological sample of one or more individual(s) capable of producing a spontaneous anti-TERT CD4 Th immune response. It may be a statistical reference value.

In a particular embodiment, the method may involve isolating and optionally culturing the CD4+ T cells either before or after stimulation by the peptide, polypeptide or the conjugate of the invention. The subset of cells that are specific of the peptides of the invention is then quantified, e.g. by IFN-γ ELISPOT. Details of an exemplary protocol are given in the Experimental section. Flow cytometry may also be used, e.g. by following a standard protocol of intracytoplasmic cytokine staining (see e.g. Prussin and Metcalfe, Journal of Immunological Methods, 1995, 188: 117-128).

In addition, the UCP-based immunomonitoring of the invention can be used to provide compensatory measures to restore and/or improve anticancer immune responses. The peptides of the invention can be effective tools for monitoring a CD4 Th, especially CD4 Th1, immune response. More particularly, the peptides(s) or the conjugate(s) of the invention can be used to determine the level of anti-telomerase CD4 Th cell and to consequently adapt the adjuvant therapy, preferably the anti-tumoral treatment described herein (i.e. the administration of the pharmaceutical composition comprising the peptide(s) of the invention or a nucleic acid encoding said peptide(s), or a conjugate comprising said peptide(s)). More precisely, the pharmaceutical composition of the invention can be used ever to establish a non-existent anti-telomerase CD4 Th response or to boost a preexistent anti-telomerase CD4 Th response in a patient.

It is thus described a method of monitoring whether a patient is in need of an adjuvant therapy or an adjusted adjuvant therapy, that is preferably a pharmaceutical composition comprising the peptide(s) of the invention or a nucleic acid encoding said peptide(s), which method comprises stimulating Peripheral Blood Mononuclear Cells (PBMC) obtained from a biological sample of the patient with a peptide, polypeptide or a conjugate of the invention, and determining the level of CD4 Th cells that are specific for the peptide, polypeptide or the conjugate, wherein a level of CD4 Th cells inferior to a control value is indicative of a patient in need of treatment adjusting.

According to this aspect of the invention, the "control value" is established from the level of anti-TERT CD4 Th1 cells of a biological sample of said patient. More precisely, the level of anti-TERT CD4 Th1 cells in a patient having a tumor is determined at different times of his treatment (e.g. before, during and/or after chemotherapy) and the previous value(s) are considered to be the "control value(s)" to adapt the treatment.

The peptides or polypeptides of the invention can be further used as markers to establish a prognosis and predicting survival of a patient having a tumor.

In a particular embodiment, it is further disclosed a in vitro method for predicting the outcome of a patient having a tumor, which method comprises stimulating Peripheral Blood Mononuclear Cells (PBMC) obtained from a biological sample of the patient with a peptide, polypeptide, or a conjugate of the invention, and determining the level of CD4 Th cells that are specific for said peptide or said conjugate, wherein a level of CD4 Th cells inferior to a control value is indicative of a patient likely to relapse.

According to this aspect of the invention, the patient can be undergoing a conventional therapy, as described above, or being treated with a pharmaceutical composition comprising the peptide(s) of the invention or a nucleic acid encoding said peptide(s) or a combination of said conventional therapy and said pharmaceutical composition.

According to this aspect of the invention, the "control value" may be established from the level of anti-TERT CD4 Th cells in a biological sample of one or more patient(s) having a tumor for which a favorable prognostic has been predicted by any other methods known in the art. It may be a statistical reference value.

The peptides of the invention can be further used as markers to determine the responsiveness of a patient, especially a patient having a tumor, to a conventional therapy. According to this aspect of the invention, the UCP-specific immunity response is quantified before, during and after a conventional therapy, to determine if the patient is a responder or a non-responder to said conventional treatment.

It is thus described an in vitro method for monitoring a response to a conventional therapy in a patient, which method comprises stimulating Peripheral Blood Mononuclear Cells (PBMC) obtained from a biological sample of the patient with a peptide, polypeptide, or a conjugate of the invention, and determining the level of CD4 Th cells that are specific for said peptide, polypeptide, or said conjugate, wherein a level of CD4 Th cells inferior to a control value is indicative of a poor response to said conventional therapy.

According to this aspect of the invention, the "control value" is established from the mean of the level of anti-TERT CD4 Th1 cells of a biological sample of a group of patients having a tumor that are not responsive to said conventional therapy and of a group of patients that are responsive to said conventional therapy.

Further aspects and advantages of the present invention will be disclosed in the following experimental section, which should be regarded as illustrative and not limiting the scope of the present application.

LEGENDS TO THE FIGURES

The patent or application file contains at least one drawing executed in color. Copies of this patent or patent application publication with color drawing(s) will be provided by the Office upon request and payment of the necessary fee.

FIG. 1: UCP-specific T cell lines obtained from healthy donors.

CD4 T cell lines were obtained from PBMCs of healthy donors after three rounds of stimulation with a mixture of the four UCP and IFN-γ-producing CD4 T cells were assessed by ELISPOT. (A) Responses against individual UCPs are shown for six healthy donors. (B) UCP-specific T cell lines were stimulate with the relevant peptide in presence of anti-HLA class I (W6.32), HLA-DR (L243) or HLA-DP (B7/21) blocking antibodies (C) Responses against individual UCPs for three healthy donors with various HLA-DR genotype.

Figure 2:
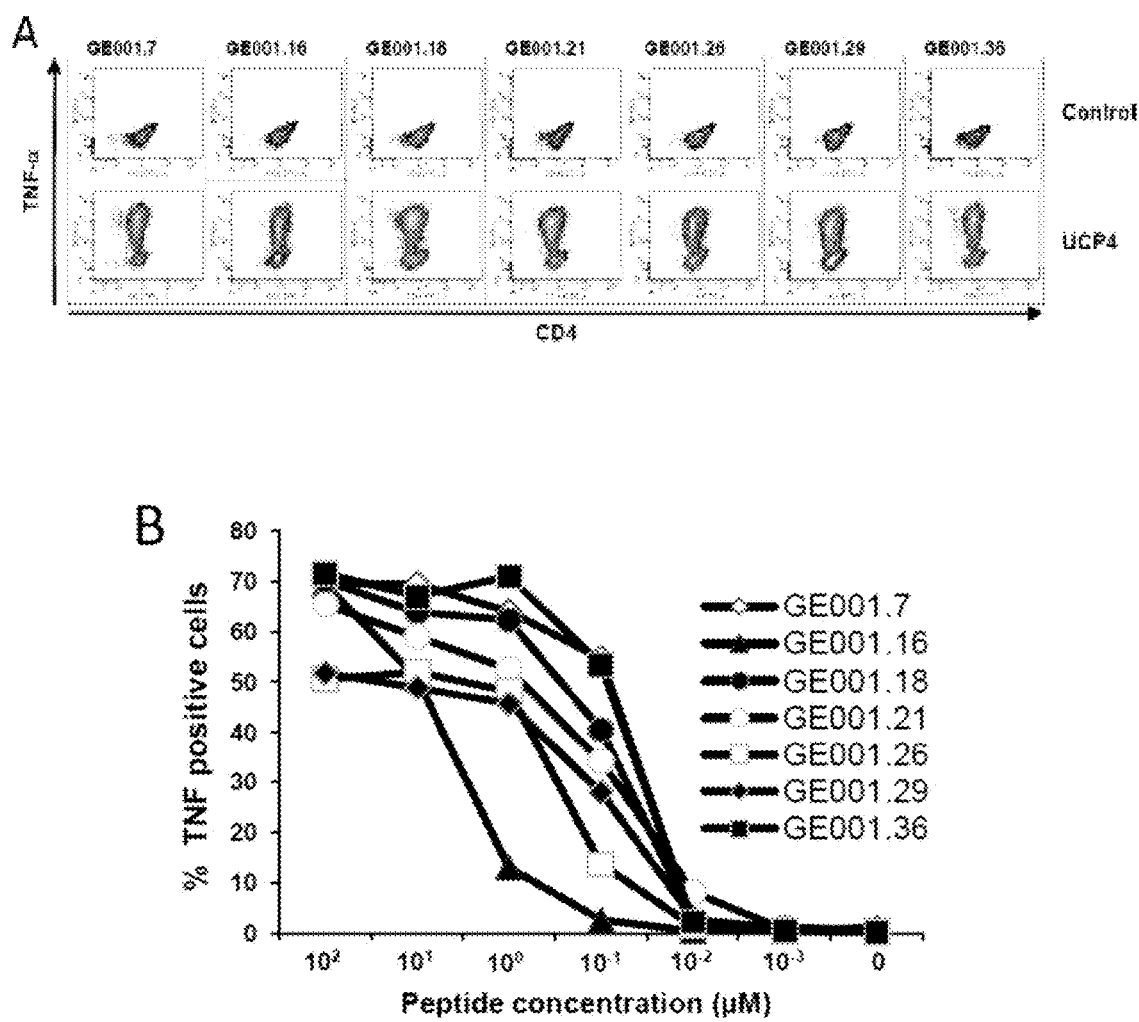
Figure 2:
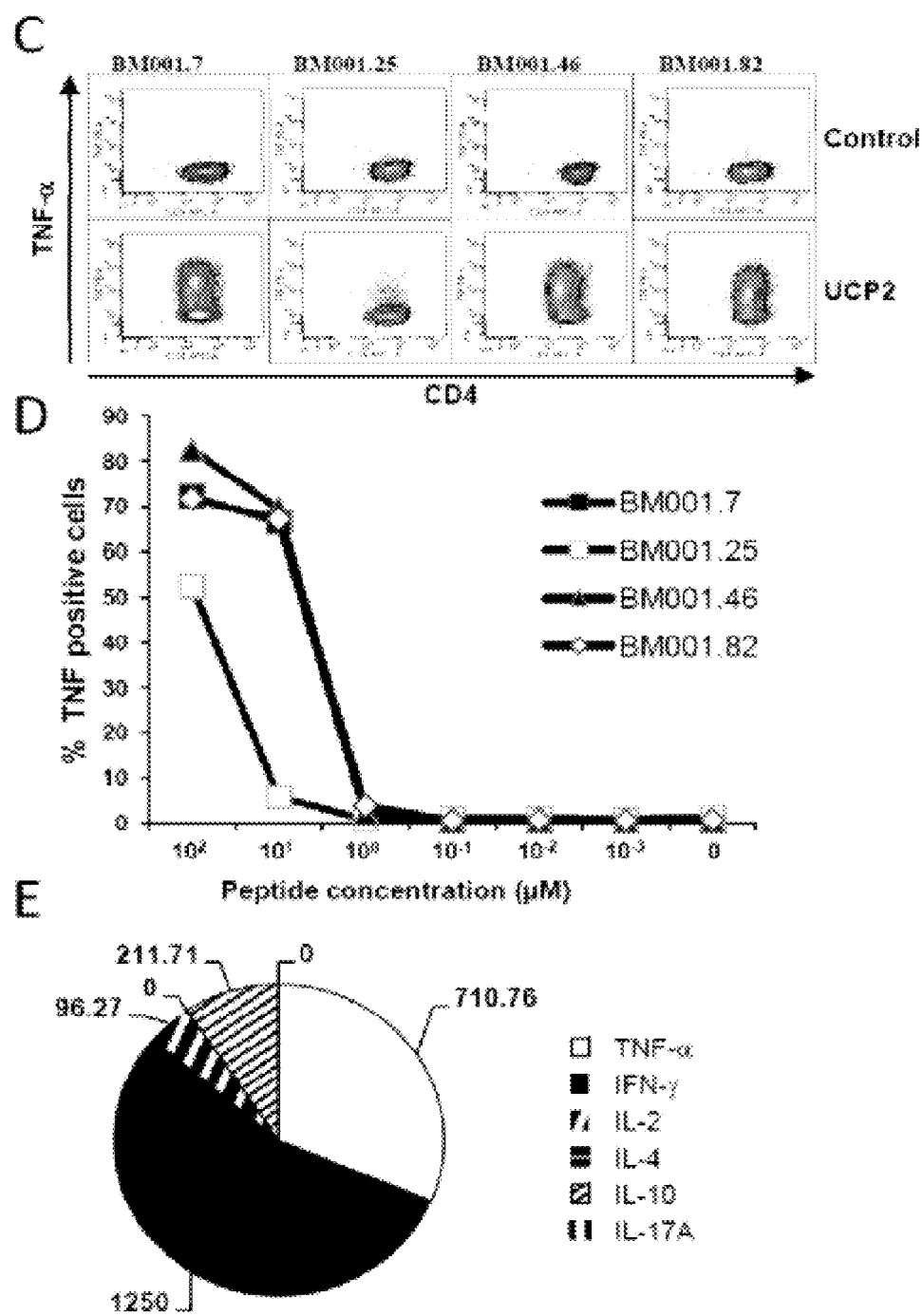

FIG. 2: Functional characterization of UCP-specific CD4 T cell clones.

T cell clones were obtained by limiting dilution of cancer patients T cell lines stimulated one time with the pool of UCPs. (A and C) Percentage of TNF-producing T cells and of T cell clones isolated from patients GE001 in response to 10 μM of the relevant UCP; $10^5$ T cells were incubated for 5 h in the presence of Brefeldin A, stained with CD4 antibody, fixed, and stained with anti-TNF antibody in a permeabilization buffer; $10^4$ T cells were then analyzed in flow cytometry. (B and D) Reactivity of the CD4 T cell clones in response to relevant UCP. CD4 T cell clones were culture with a range of the indicated peptide concentration. TNF secretion was assessed 5 h in the presence of Brefeldin A, by flow cytometry. (E) Detection of cytokines produced by GE001.36 T cell clone in response to 10 μM of UCP4 using human ten-plex cytokines assay.

Figure 3:
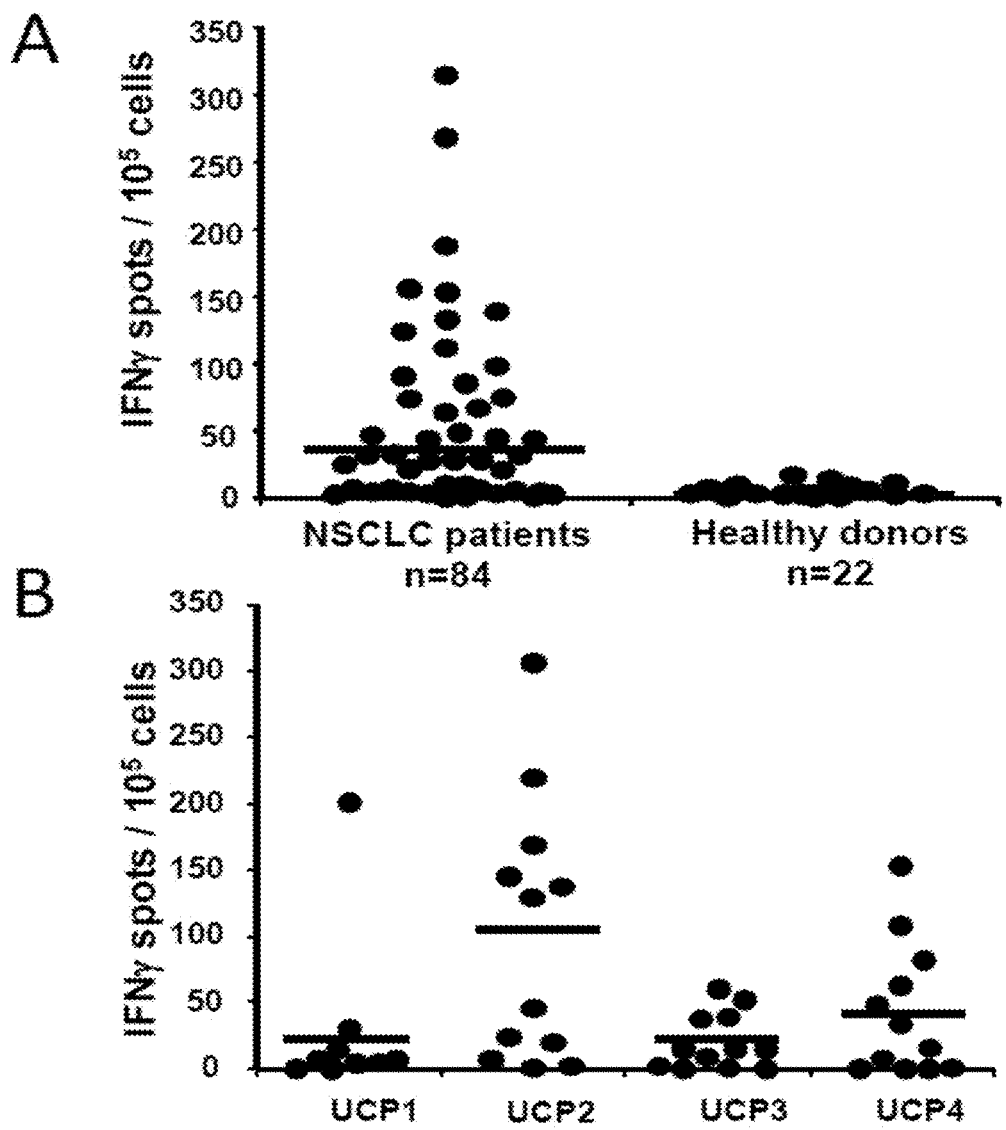
Figure 3:
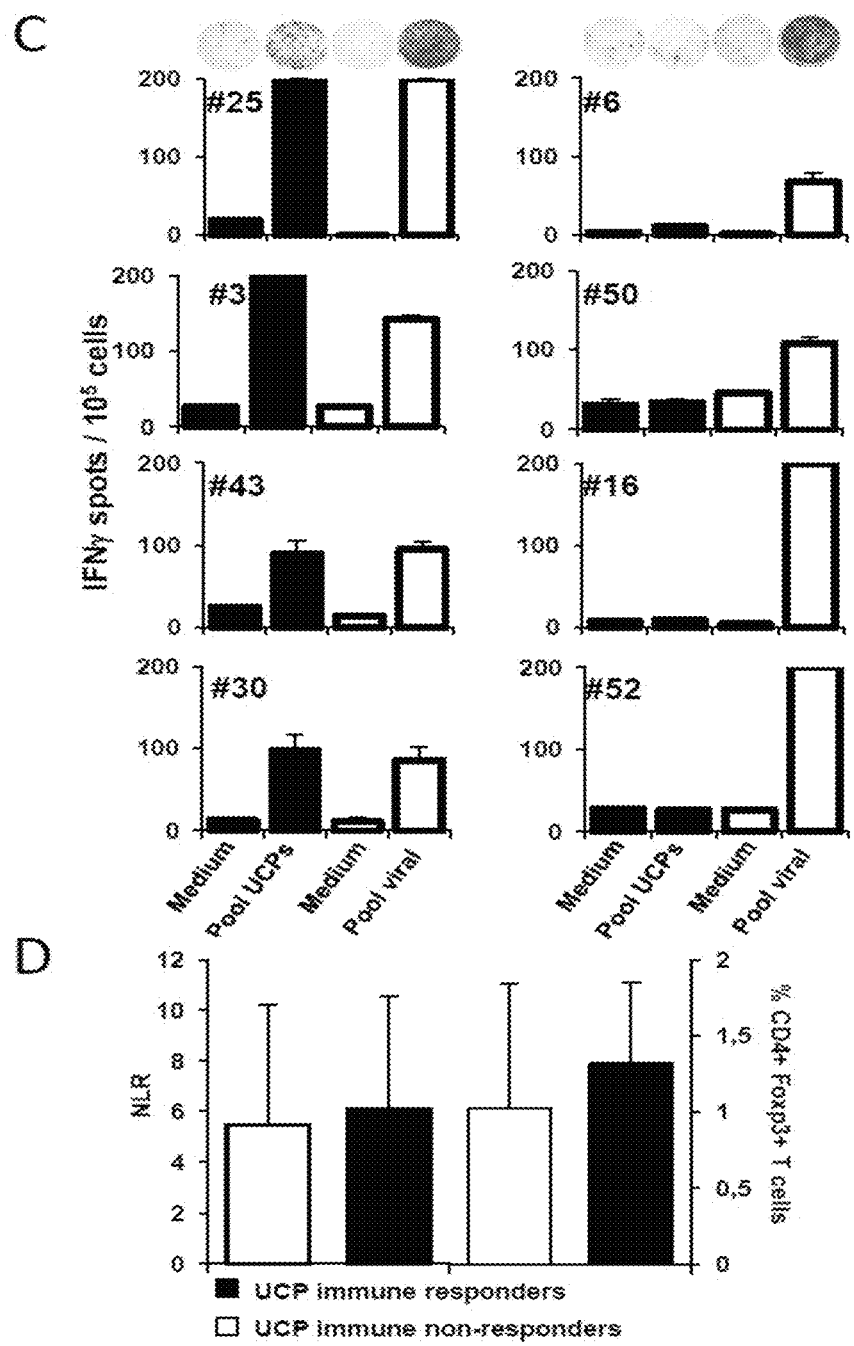

FIG. 3: Naturally occurring UCPs specific response in metastatic NSCLC patients.

(A) Spontaneous UCP specific-T cell responses were assessed in 84 NSCLC patients and 22 healthy donors as control. After short time stimulation (one week) with a mixture of the four UCPs the presence of specific-T cells was detected using IFN-γ ELISPOT assay. The results represented specific IFN-γ spots after subtraction of background. Responses were positive when IFN-γ spots were >10 and more than two fold the background (B) Frequency of individual UCP-specific T cell responses in 12 NSCLC patients was shown.

(C) Illustration of UCPs versus viral-specific immune responses in eight NSCLC patients after one week in vitro stimulation.

(D) Baseline Neutrophils on Lymphocytes Ratio (NLR) and CD4+ Foxp3+ T cell frequency in patients according to the UCP-specific immune status.

Figure 4:
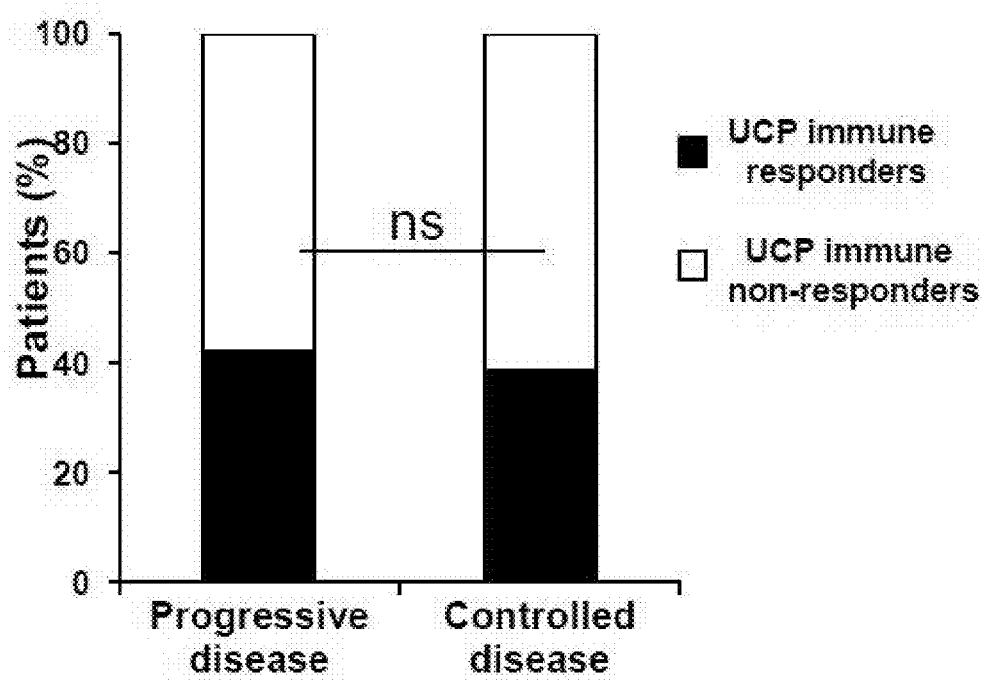
Figure 4:
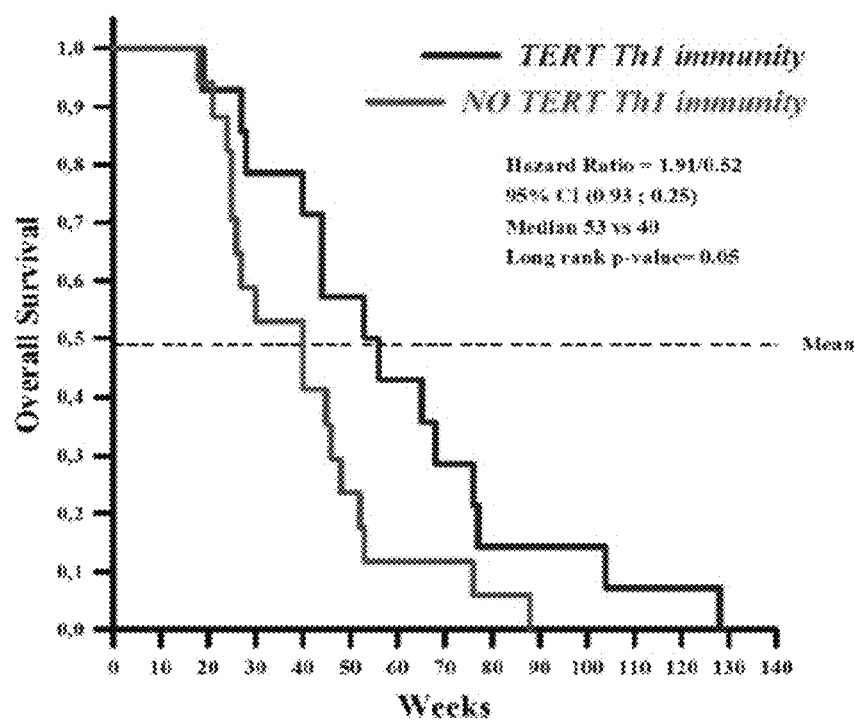
Figure 4:
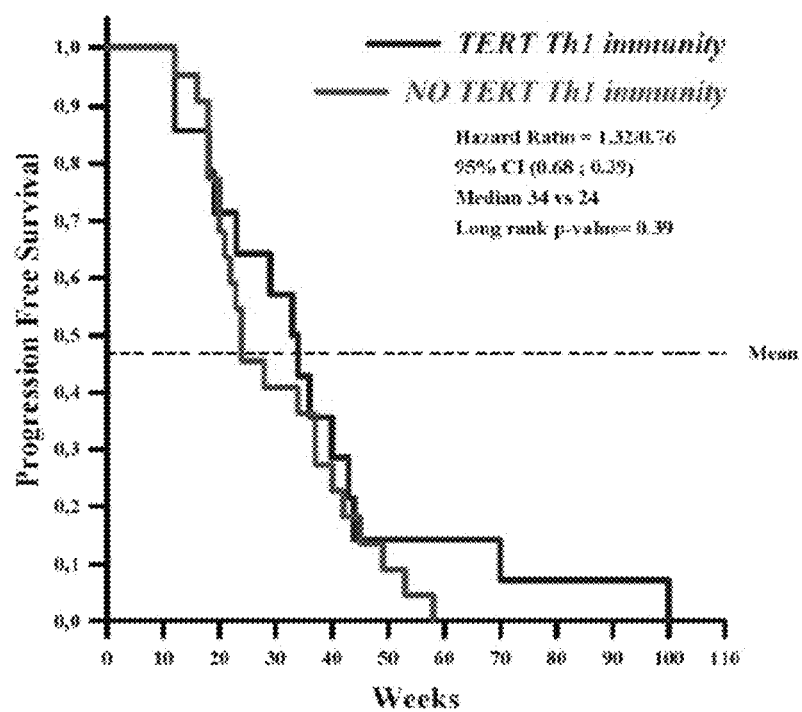
Figure 4:
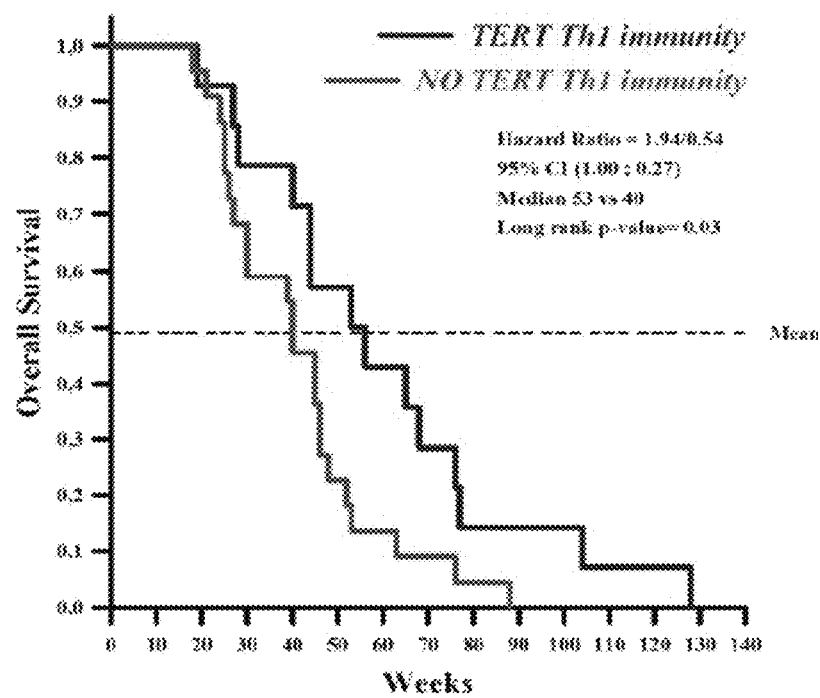
Figure 4:
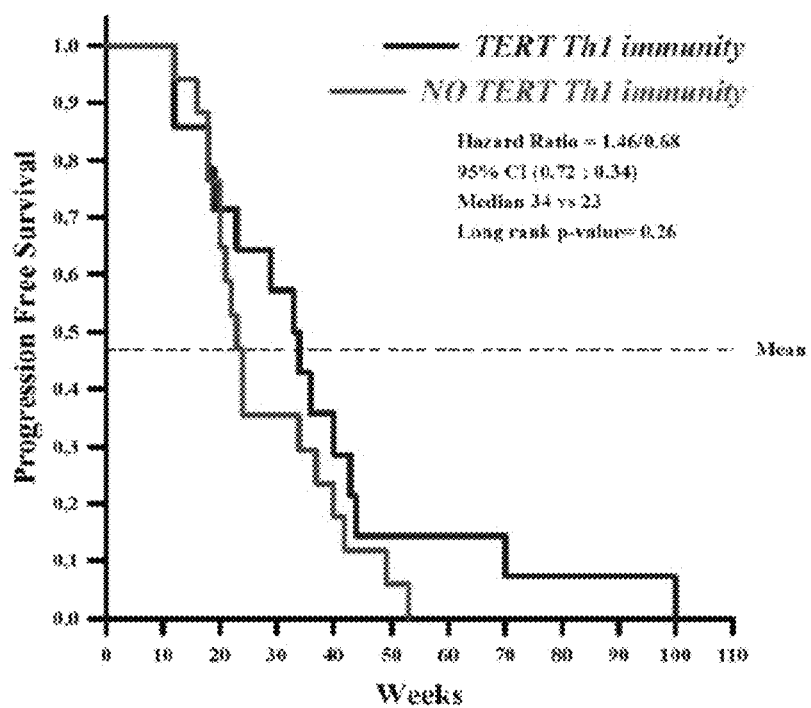

FIG. 4: Impact of spontaneous UCPs CD4 T cell response in metastatic NSCLC patients.

(A) UCPs responder and non-responder frequencies in patients with progressive disease (PD) or control disease (CD).

(B) Kaplan-Meier estimates of overall survival (OS) and (C) progression free survival (PFS) of CD patients.

(D) OS and (E) PFS of CD patients treated with platinum-based first line chemotherapy.

Figure 5:
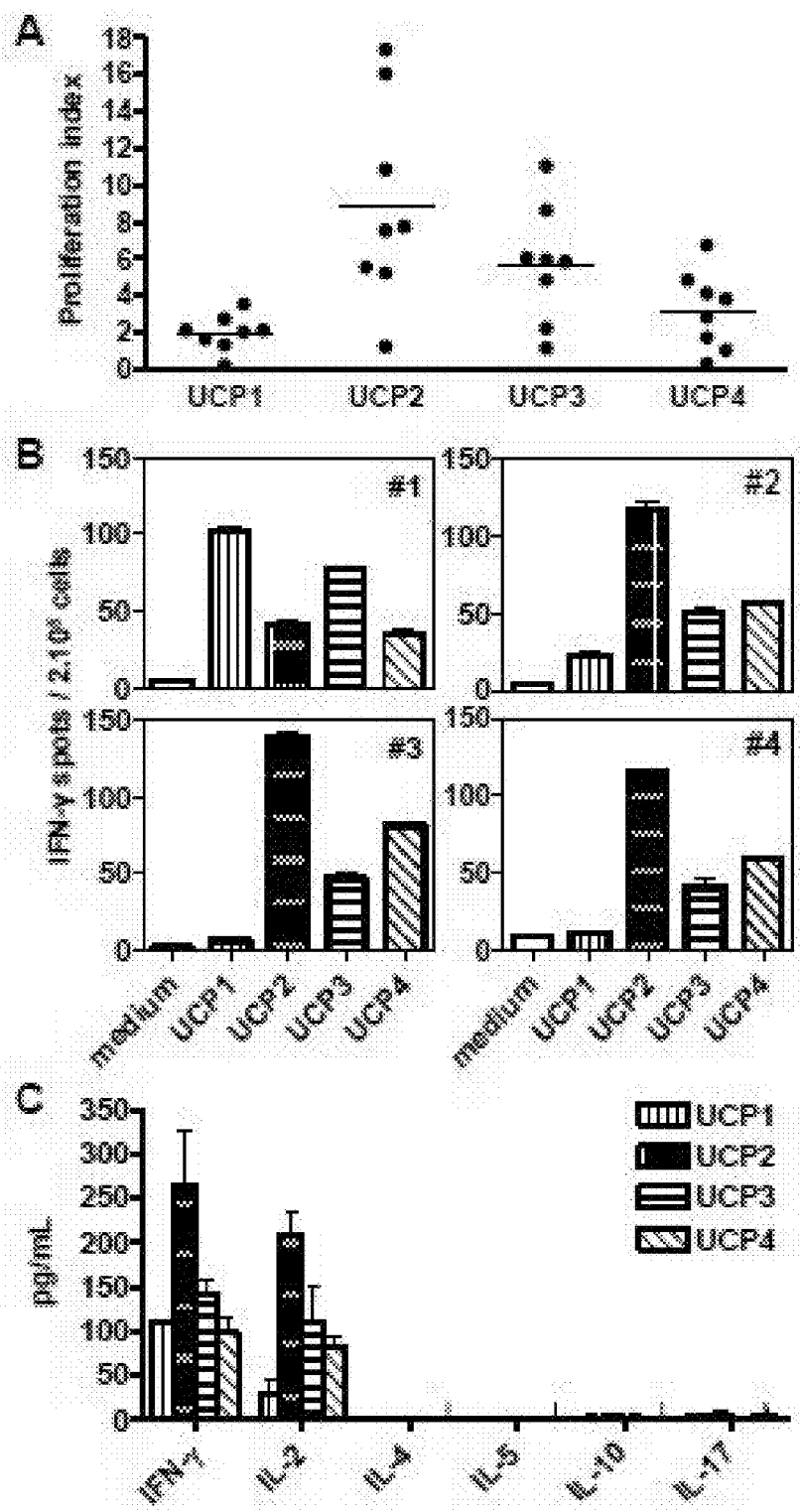
Figure 5:
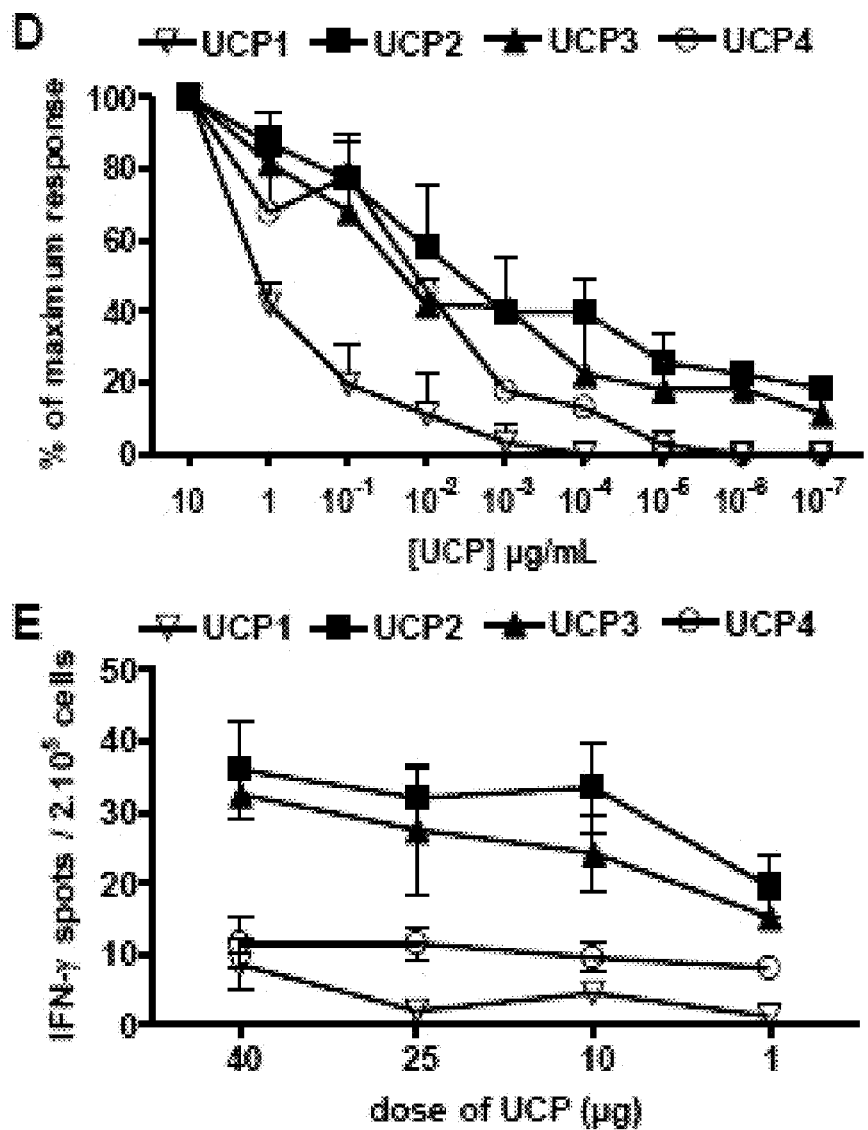

FIG. 5: UCPs vaccinations stimulate high avidity Th1 polarized CD4 T cell responses.

(A-B), A2/DR1 mice (n=8) were immunized twice with a DNA encoding TERT.

(A), Proliferation of spleen lymphocytes in presence of UCPs.

(B), CD8 depleted spleen lymphocytes from DNA-immunized mice were assayed in ex vivo IFN-γ ELISPOT. Columns mean of triplicate from 4 mice; bars, SD.

(C-D), Mice (3-4/group) were immunized once with each UCP in IFA.

(C), Ten days later, spleen-isolated CD4 T cells were cultured overnight in presence of DC loaded with UCP. The cytokines production was measured in the supernatant by Luminex assay. Columns, mean of cytokine levels; bars, SD.

(D), Isolated CD4 T cells were cultured ex vivo with increasing concentrations of peptide as indicated. IFN-γ production was measured by ELISPOT. Curves, mean responses from 3 mice, bars, SD.

(E), Mice were vaccinated once with low dose of UCP as indicated. UCP-specific T cell responses were evaluated in spleen by ex vivo IFN-γ ELISPOT.

Figure 6:
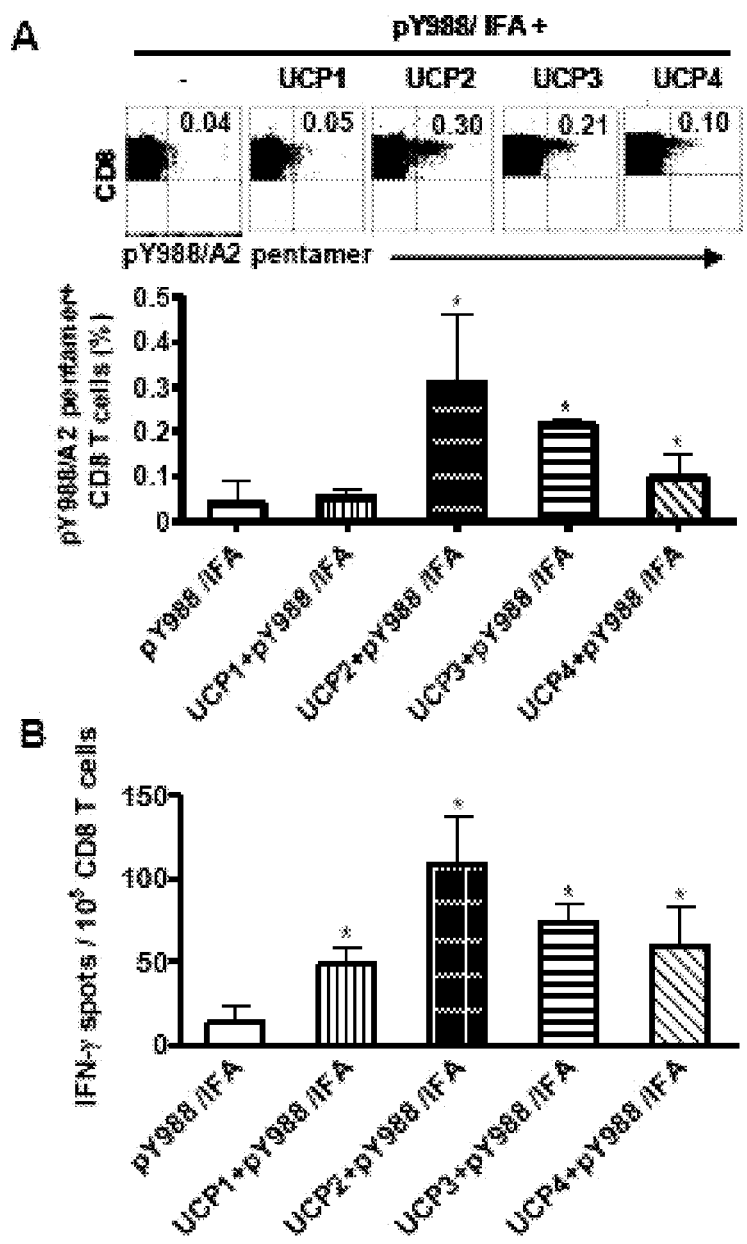
Figure 6:
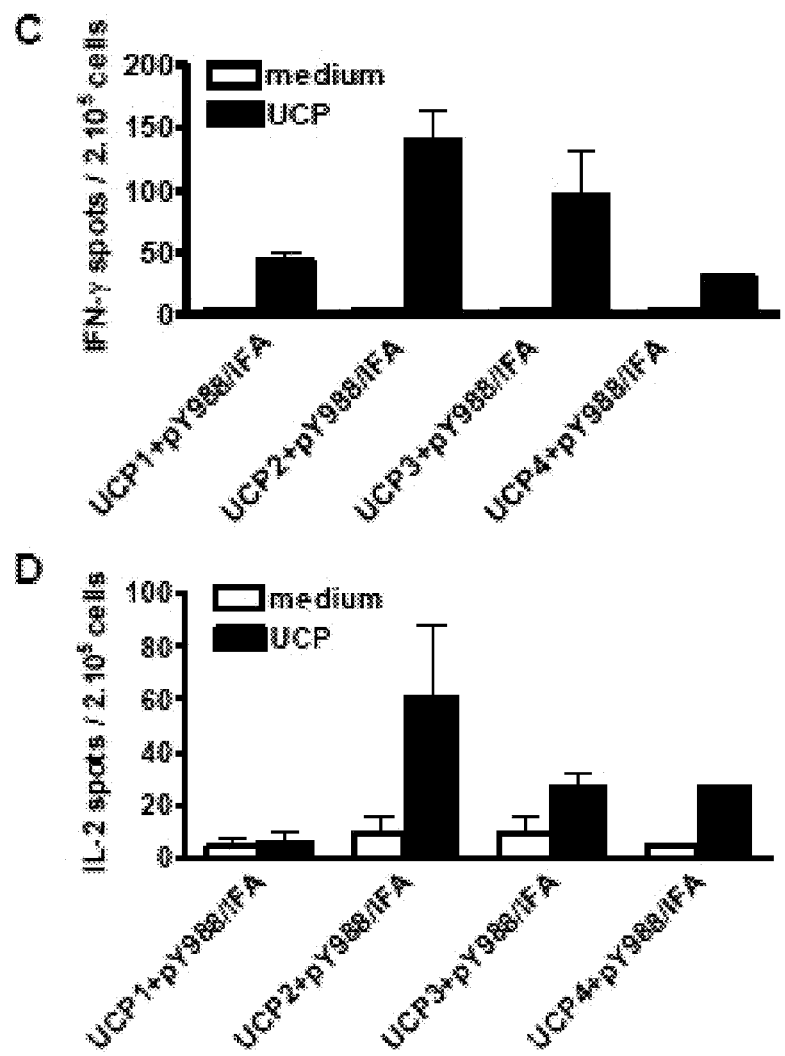

FIG. 6: CD4 helper role of UCPs vaccinations on the self/TERT-specific CTL responses Mice (3/group) were immunized either with pY988 plus each UCP in IFA or with pY988/IFA alone and the immune responses were monitored ten days later in the spleen.

A, freshly isolated CD8 T cells were stained with TERT pY988/A2+ pentamer. Representative flow cytometry dot plots (upper panel) and mean percentages of pY988/A2+ CD8 T cells (lower panel) are shown.

B, Ex vivo detection of anti-pY988 CD8 T cells by IFN-γ ELISPOT.

C-D, simultaneous UCP-specific CD4 T cell responses were assessed in CD8-depleted fraction by IFN-γ (C) and interleukine-2 (D) ELISPOT assays. Columns, mean of spots from 3 mice; bars, SD.

Data are representative of three independent experiments.

Figure 7:
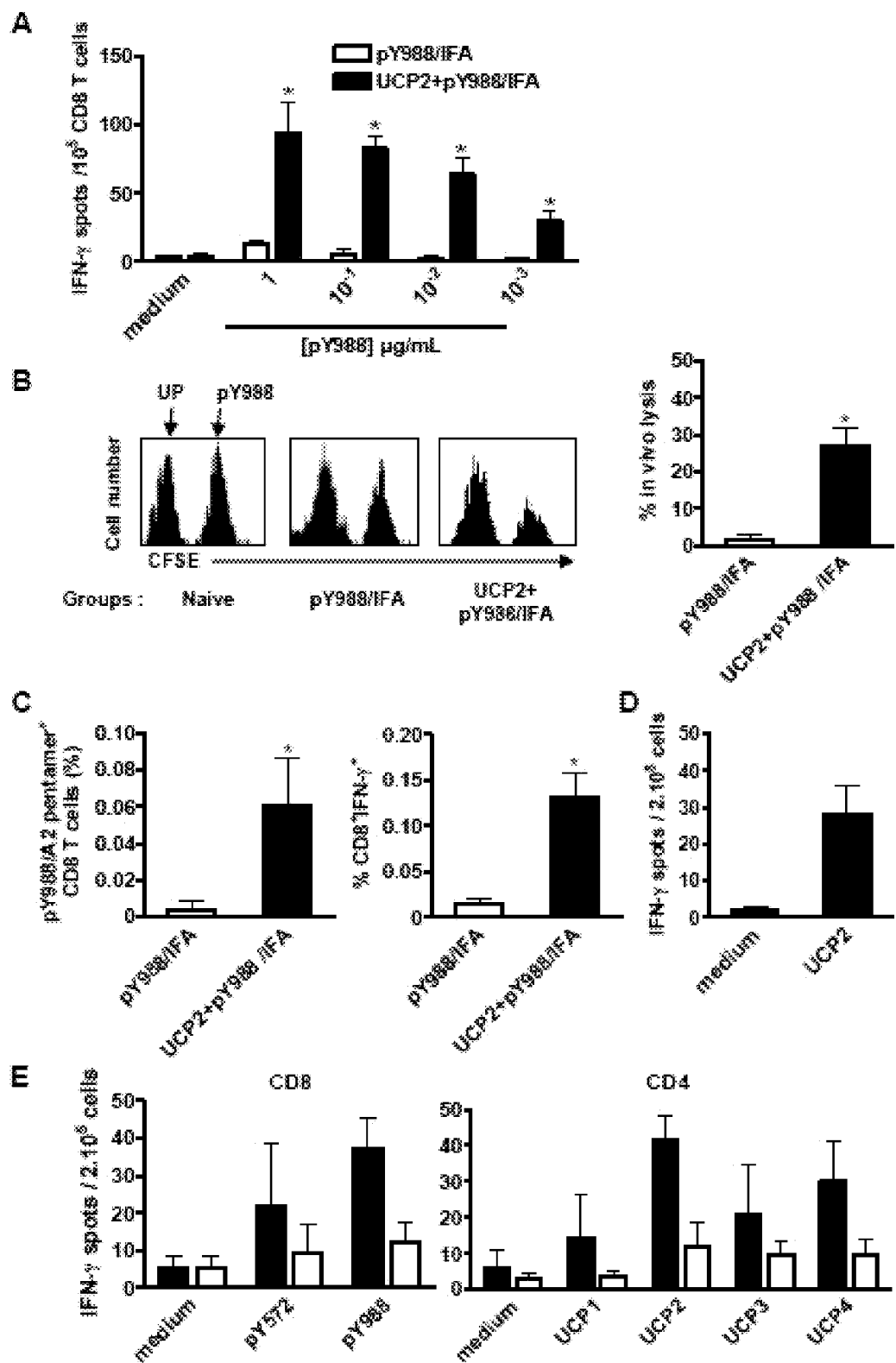

FIG. 7: Immunization in presence of UCP2 enhances the quality of self pY988-specific CTL responses.

A-C, Mice (3-4/group) were immunized once either with pY988 plus UCP2 (UCP2+pY988/IFA) or with pY988/IFA alone.

A, Ten days later, freshly isolated spleen CD8 T cells were cultured with increasing pY988 peptide concentration and IFN-γ-secreting CD8 T cells were detected by ex vivo ELISPOT.

B, In vivo cytotoxic assay. Representative flow cytometry histograms showing lysis of CFSE-labeled pY988-loaded target cells compared to unpulsed (UP) and the mean of in vivo percentage lysis are shown.

C-D, Long-term T cell responses were evaluated 30 days after immunization.

C, Frequencies of pY988/A2 pentamer+ CD8 T cells gated on CD44hiCD62lo cells (left) and by IFN-γ secretion assay (right).

D, UCP2-specific CD4 T cell response measured in CD8-depleted fraction by ex vivo IFN-γ ELISPOT.

E, Mice (4/group) were treated either with anti-CD4 mAb (GK1.5) (CD4 depleted, white bars) or with saline (non depleted, black bar) 3 days before immunization with DNA/TERT.

The self/TERT-specific CTLs (left) and UCP-specific CD4 T cell responses (right) were measured in spleen by ex vivo IFN-γ ELISPOT.

Data are representative of three independent experiments.

Figure 8:
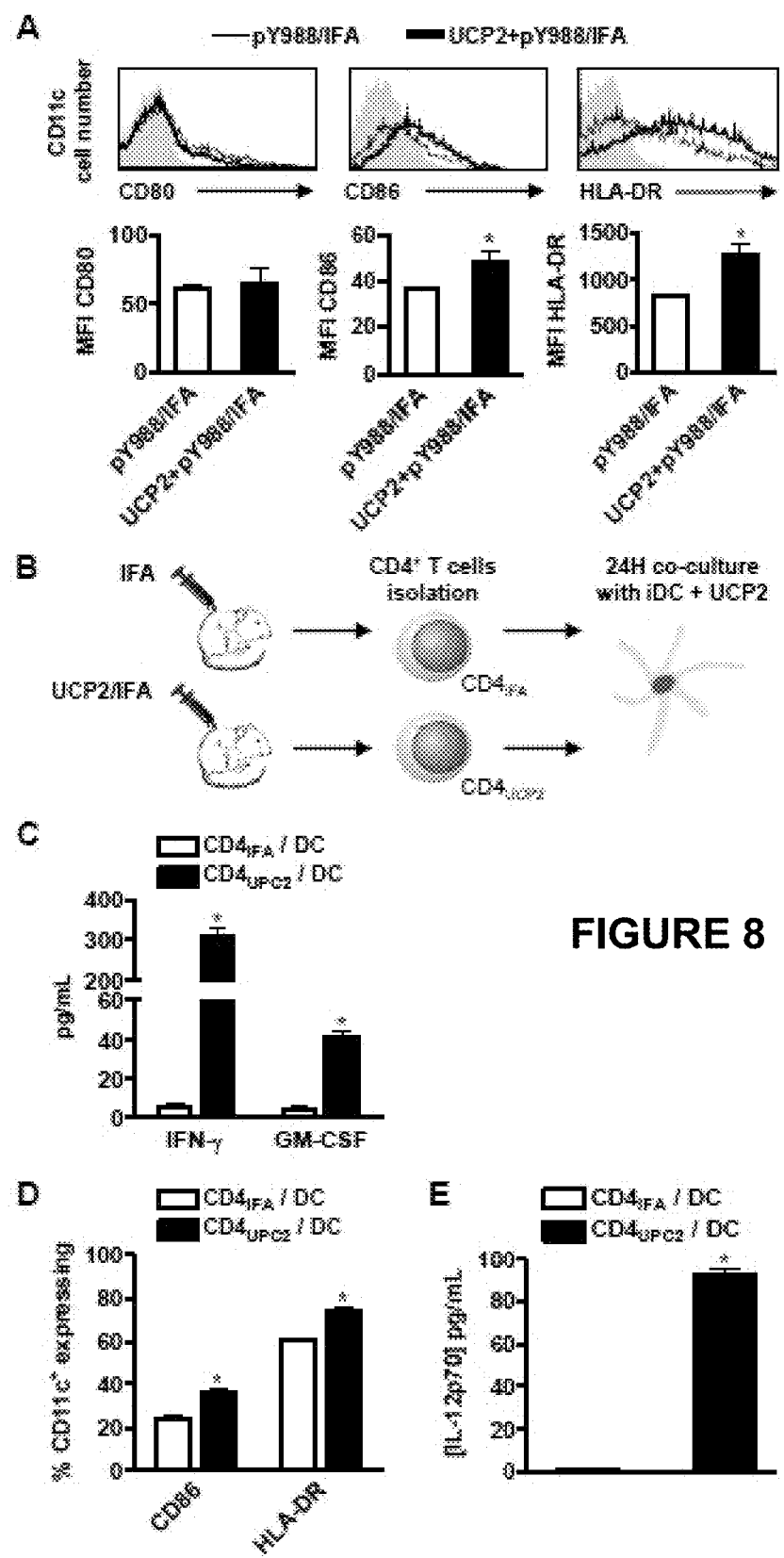

FIG. 8: UCP2-specific CD4 Th1 cells active dendritic cells.

A, Mice (3/group) were immunized once either with UCP2+pY988/IFA or pY988/IFA alone. Ten days later, the expression of activation markers CD80, CD86 and HLA-DR were analyzed on lymph nodes CD11c+ DC by flow cytometry. Representative Flow cytometry histograms (upper panels) and the mean of MFI (lower panels) are shown. Columns, mean of MFI; bars, SD. B-E: Analysis of DC and CD4 T cells cross talk.

B, Schema of the in vitro DC-CD4 T cell co-culture.

C, IFN-γ and GM-CSF production measured by ELISA in the supernatant.

D, Expression of CD86 and HLA-DR on CD11c+ DC.

E, Interleukin 12 production measured in supernatant by ELISA.

Data are representative of two independent experiments.

Figure 9:
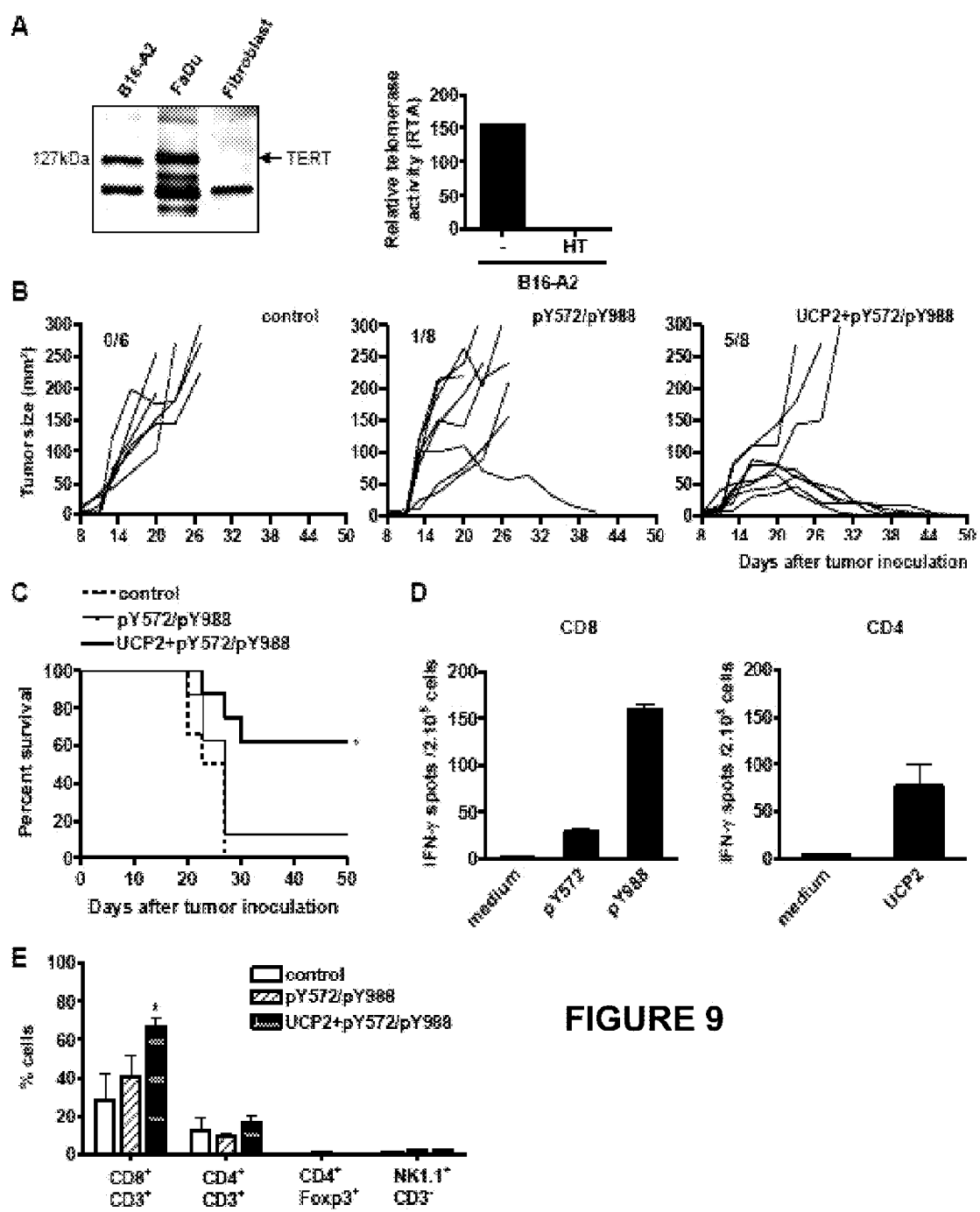

FIG. 9: Therapeutic antitumor effect of UCP-based vaccination.

A, TERT expression by western-blot (left) and activity by TRAP-ELISA assay (right) in B16-A2 melanoma.

B-E. Tumor-bearing mice (6-8 mice/group) were therapeutically vaccinated with peptides as described (materials and methods).

B, Follow-up of tumor size. The numbers in parentheses indicate mice with tumor regression per group.

C, Survival curves recorded until 50 days.

D, Detection of anti-TERT immune responses in the spleen of tumor free mice from UCP2-vaccinated group by IFN-γ ELISPOT.

E, In this experiment, tumor-bearing mice (n=4/group) were vaccinated as above and tumor-infiltrating immune cells were analyzed at day 25 by flow cytometry. Columns, mean of percentages of cells; bars, SD.

Data are representative of two independent experiments.

Figure 10:
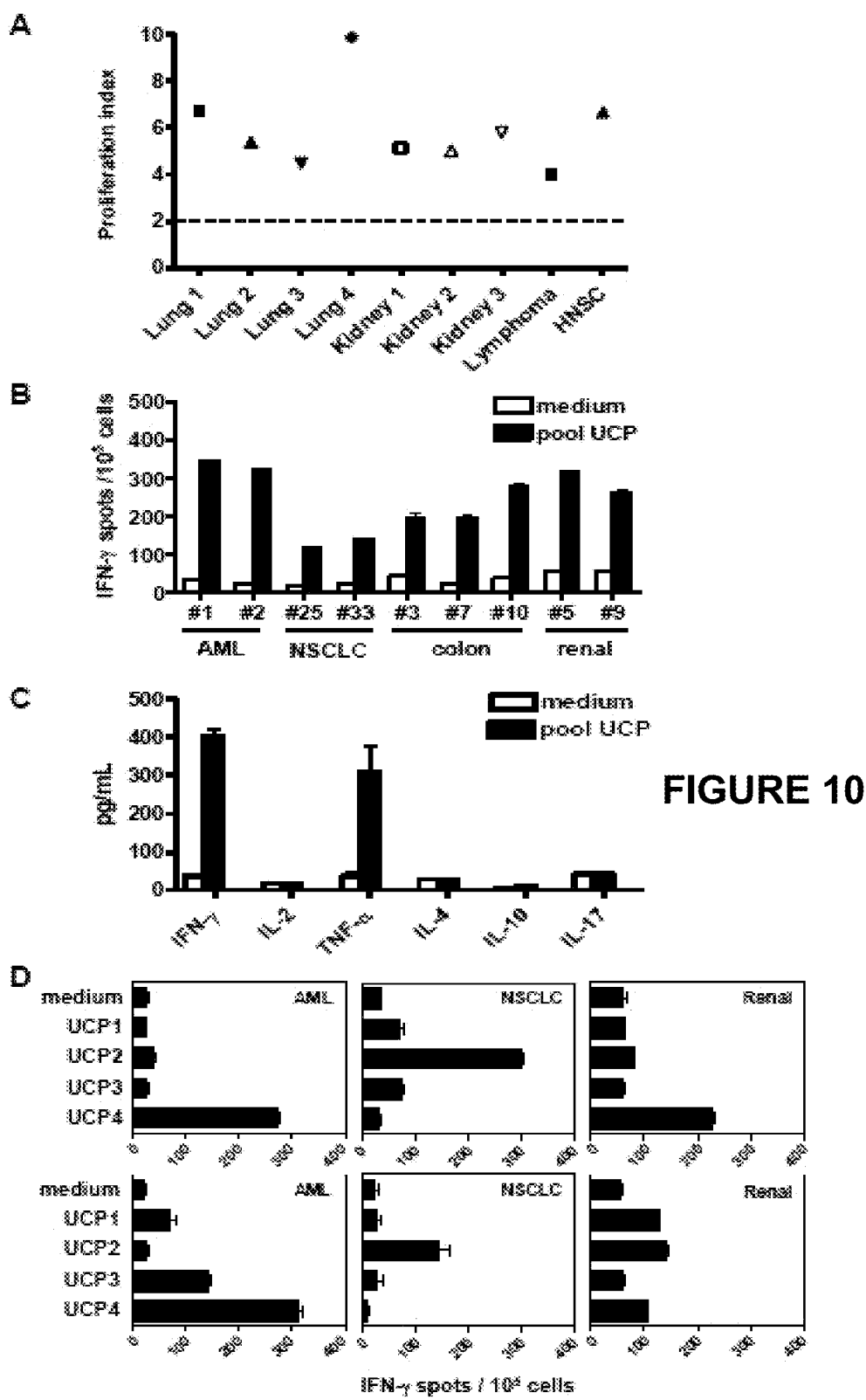

FIG. 10: Analysis of UCP-specific T cell responses in human.

A, Blood lymphocytes from cancer patients were directly cultured with pool of UCPs during five days and specific proliferation was measured by 3H thymidine incorporation. Representative data from nine responding patients are shown.

B-D, Lymphocytes were cultured in vitro with pool of UCPs for one week.

B, Detection of UCP-specific T cell by IFN-γ ELISPOT. Representative data from nine responding patients are shown. Columns, mean of triplicate; bars, SD.

C, Detection of cytokine production by DIAplex assay in supernatant after 15 h of culture in presence of UCPs. Columns, mean cytokine levels from three patients; bars, SD. D, T cell responses against individual UCP for six responding patients.

Figure 11:
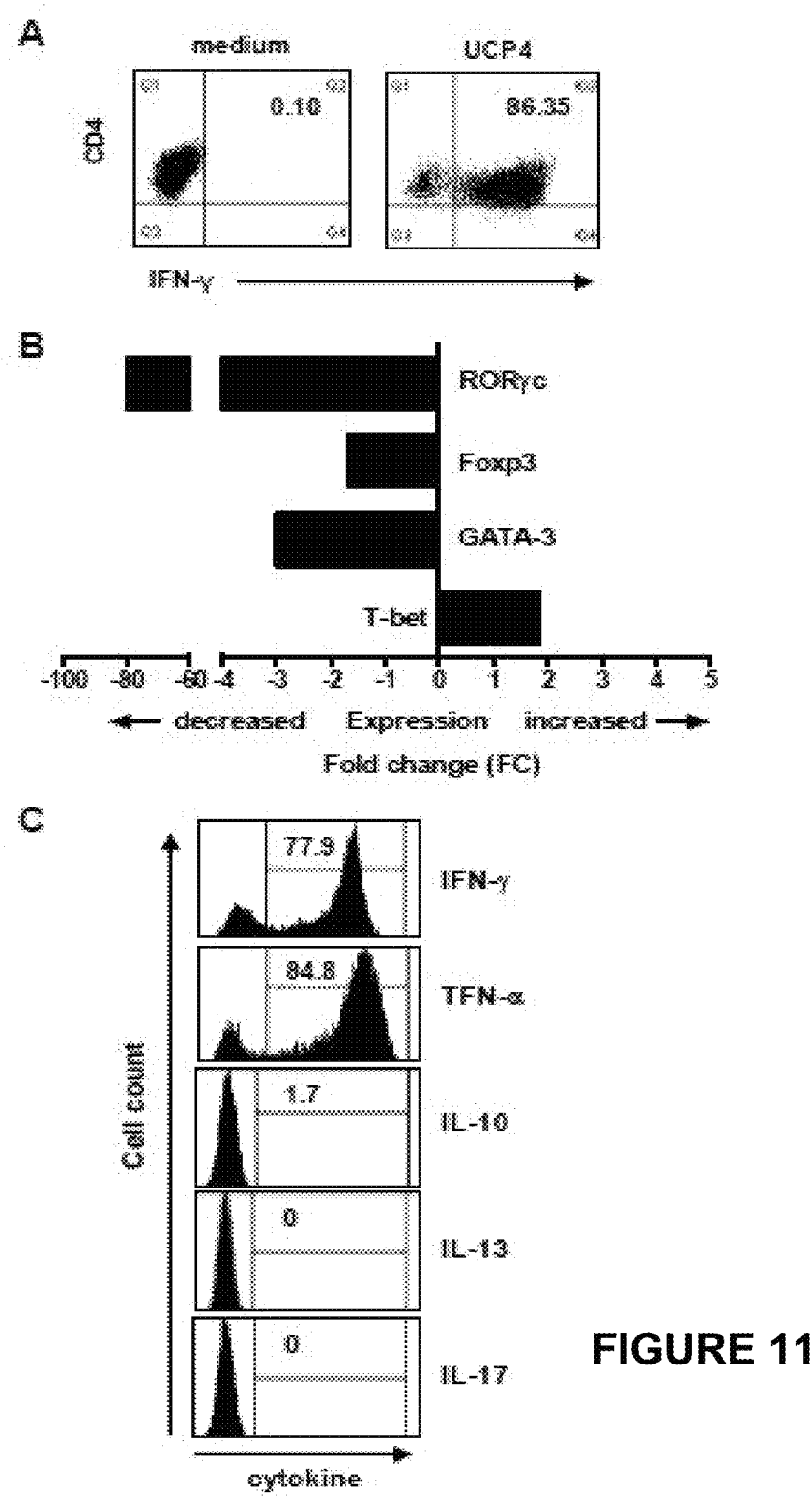

FIG. 11: Isolation of UCP4-specific CD4 Th1 cell clone from a cancer patient.

A, IFN-γ producing UCP4-specific T CD4 cell clone was isolated from a colorectal cancer patient.

B, Evaluation of mRNA expression of UCP4-specific T CD4 clone by real-time RT-PCR.

Positive and negative fold change values indicate the up- or down-regulation of mRNA expression compared to CD4 T cells from a healthy volunteer.

C, Analysis of cytokines production by intracellular staining.

EXAMPLES

Example 1

Identification of Promiscuous HLA-DR Telomerase-Derived Epitopes and Analysis of Spontaneous Tumor-Specific CD4 T Cell Immunity in Lung Cancer Patients 1.1 Materials and Methods
Patients Patients were enrolled at the university hospital Georges Pompidou (Paris, France) and university Hospital Jean Minjoz (Besancon, France) from January 2009 to February 2011. Tumor stage and grading were determined according to the International Union against Cancer (UICC) classification. After informed consent, patients with histologically proven NSCLC were prospectively included in the clinical trial. This study was conducted in accordance with French laws and after approval by the local ethics committee. Blood cells were collected from anonymous healthy donors at the Etablissement Francais du Sang (EFS, Besancon, France) as apheresis kit preparations after informed consent and following EFS guidelines. HLA-DR genotyping was performed by using the Olerup SSP DRB1 typing kit (Olerup, Sweden).

Telomerase-Derived CD4 T Epitopes Selection and Binding Assay

The four peptides derived from TERT referred as Universal Cancer Peptide (UCP1 (PAAFRALVAQCLVCV, SEQ ID NO:4), UCP2 (KSVWSKLQSIGIRQH, SEQ ID NO:1), UCP3 (GTAFVQMPAHGLFPW, SEQ ID NO: 2) and UCP4 (SLCYSILKAKNAGMS, SEQ ID NO:3) were predicted in order to bind multiples HLA-DR molecules by using SIFPETHI (accessible via World Wide Web at syfpeithi.de), NetMHCpan 2.1 (accessible via World Wide Web at cbs.dtu.dk/services/NetMHCII/) and NetMHCII 2.2 (accessible via World Wide Web at cbs.dtu.dk/services/NetMHCII/) softwares (Kobayashi et al, 2008). Synthetic peptides (>80% purity) were purchased from Activotec (Cambridge, United Kingdom). The binding capacity to HLA-DR molecules was assessed by competitive ELISA as previously reported (Wang et al).

Generation of UCP-Specific T Cell Lines from Healthy Donors

Peripheral Blood Mononuclear Cells (PBMC) were isolated by density centrifugation on Ficoll-Hyperpaque gradients (Sigma-Aldrich, France) and plated at $4.10^6$ cells per well in a 24-well plate in RPMI 5% human serum with 10 µM of pool of the four UCPs. Recombinants interleukin 7 (5 ng/mL) (Peprotech, France) and interleukin 2 (20 UI/mL) (Novartis, Switzerland) were added day 1 and day 3 respectively. At day 7 and 14, cells were stimulated with γ-irradiated autologous PBMC pulsed with 10 µM of UCPs and 20 UI/mL IL-2 was added at day 8 and 15 as previously reported (Wang et al, Adotevi et al, 2006). At day 21, CD4 T cells were purified (Miltenyi, France) and the specificity of T cell lines was investigated by IFN-γ ELISPOT. Briefly, CD4 T cells ($10^5$/well) were cultured in anti-human IFN-γ mAb precoated ELISPOT plate with each UCP (5 µM) in AIM V medium (Invitrogen, United Kingdom) for 18 h at 37° C. Cells cultured with medium alone or PMA (100 ng/ml) (Sigma-Aldrich) and ionomycin (10 µM) (Sigma-Aldrich) were used as negative and positive controls, respectively. The IFN-γ spots were revealed following the manufacturer's instructions (Gene Probe, France). The number of specific T cells expressed as spot-forming cells/$10^5$ cells was calculated after subtracting negative control values (background). Spot-forming cells were counted using the C.T.L. Immunospot system (Cellular Technology Ltd., USA). For HLA-DR-restriction, the following blocking antibodies anti-HLA-class 1 (clone W6.32), HLA-DR (clone L243) and HLA-DP (clone B7/21) (10 µg/ml) were added in cell culture during the ELISPOT. All the experiments were performed in triplicates.

CD4 T Cell Clones Isolation and Amplification

T Cells Clones were Isolated by Limiting Dilution and Amplified after Stimulation by PHA in presence of irradiated allogenic PBMC, B-EBV cell line and 150 UI of interleukin 2 according to previously described procedure (Godet et al). Functional analyses of UCP-specific CD4 T cell clones were performed by using intracytoplasmic TNF-α staining and Human Ten-plex cytokines assay (Human Th1/Th2/Inflammation Diaplex, Diaclone, France).

Assessment of Spontaneous UCP-Specific CD4 T Cell Responses

Ficoll-isolated PBMC from cancer patients or healthy volunteers were cultured with 10 µM of pool of UCPs in a 24-well plate ($4.10^6$ cells per well) in RPMI 5% human serum and interleukin 7 (5 ng/mL) and interleukin 2 (20 UI/mL) were added day 1 and day 3 respectively. For the recall response against viruses, cells were similarly cultured with the mix of 32 peptides from cytomegalovirus, influenza virus and Epstein Barr virus (CTL, Germany). After one week cell culture, the presence of UCP-specific T cells was measured by IFN-γ ELISPOT as detailed above.

Flow Cytometry

For intracytoplasmic cytokine staining, after a 5-h stimulation period with or without 10 µM peptide, T cells were labeled with anti-CD4 (BD Bioscience, USA) and anti-TNF-α (ebioscience, USA) using Cytofix/Cytoperm KIT (BD Bioscience). For flow cytometry Treg analysis, PBMC were first stained with surface antibodies (anti-CD4, anti-CD25, fixed, permeabilized, and then stained with anti-hFoxp3 (PCH101; eBioscience). Samples were acquired on a FACS Canto II (BD Biosciences) and analyzed with the DIVA software. NLR was defined as the absolute neutrophil count divided by the absolute lymphocyte count (Suzuki et al).

Statistics

Statistical analyses were performed with NCSS 2007 software (Number Cruncher Statistical Systems, Kaysville, USA). The level of significance was set at $p<0.05$ for all tests. Variables were expressed as a mean±SD or median, and tested with the Wilcoxon Rank-Sun test when suited. Survival curves were calculated with the Klapan-Meier method and compared with the Log-rank test.

1.2. Results

Identification of Universal HLA-DR-Restricted CD4 T Cell Epitopes from TERT

To predict the existence of CD4 epitopes within the amino acid sequence of TERT capable of binding to multiple HLA-DR molecules, the inventors have combined results from three algorithms Syfpeithi, NetMHCpan-2.1 and NetMHC2.2. They have selected four 15-mers peptide sequences referred as UCP1 to UCP4 that scored high in the probability scale for their binding capacity to the commonly found human HLA-DR alleles (Table 1). To confirm this result, the inventors have performed an in vitro binding assay based on competitive ELISA as previously reported. The data have been presented as relative affinities (RA) to easily compare their binding properties to high-binder peptides that the inventors have used as references and the strong binders have a relative affinity <100. Results confirm the ability of all the peptides to effectively bind to the most common alleles encoded by the HLA-DR (Table 5). Data are expressed as relative activity RA (ratio of the IC50 of UCPs to the IC50 of the reference peptide) and are the means of three experiments. Good binders have a RA<100 and weak binder are RA>50.

TABLE 5

Relative affinities of the peptides towards the
most common alleles encoded by the HLA-DR locus

| Peptides | SEQ ID NO: | HLA-DR alleles | | | | | | | | | |
|---|---|---|---|---|---|---|---|---|---|---|---|
| | | DR1 | DR3 | DR4 | DR7 | DR11 | DR13 | DR15 | DRB3 | DRB4 | DRB5 |
| UCP44 (UCP1) | 4 | 3 | 0.4 | 50 | 3 | 25 | 1 | 4 | 30 | 4 | 1 |
| UCP578 (UCP2) | 1 | 0.2 | 144 | 112 | 1 | 4 | 231 | 8 | 154 | 229 | 1 |
| UCP916 (UCP3) | 2 | 0.1 | 173 | 2 | 2 | 0.2 | 134 | 0.2 | 53 | >500 | 0.2 |
| UCP1041 (UCP4) | 3 | 0.3 | >500 | 34 | 8 | 0.3 | >500 | 3 | 154 | >500 | 0.5 |

The four peptides exhibited a strong capacity to bind seven different HLA-DR molecules including DR1, DR4, DR7, DR11, DR15, DRB3 and DRB5. Particularly, UCP1 and UCP2 were able to bind every HLA-DR molecules tested with RA from intermediate (100-500) to low RA (<100). Thus, according to phenotypic frequencies of the 10 prevalent HLA-DR antigens, these peptides could cover more than 90% of population (Wang et al). Furthermore, CD4 T cell responses against UCPs have been induced in humanized HLA-DR1*0101/HLA-A2 transgenic mouse model following immunization with a DNA plasmid encoding the full length TERT protein (Adotevi et al, 2006, Pajot et al) and indicating that they are endogenously processed and presented to CD4 T cell in vivo.

Then, the ability of UCP to stimulate human CD4 T cells has been tested. For this purpose, lymphocytes isolated from peripheral blood of healthy volunteers have been in vitro stimulated using a pool of UCP and the generation of UCP-specific CD4 T cell lines has been screened using ELISPOT assay. As shown in FIG. 1A, CD4 T cells were able to recognized at least one UCP. The HLA-DR restriction of the UCPs specific CD4 T cell response has been confirmed with the inhibition of IFN-γ secretion in presence of pan HLA-DR blocking antibody (FIG. 1B). The HLA-DR spectra-typing reveals that the HLA-DR alleles of normal individual were not shared supporting the promiscuous nature of the UCPs (FIG. 1C). Thus, these results imply that precursor CD4 T cells against UCPs are present in human peripheral T repertoire and they recognize these peptides in multiple HLA-DR contexts. To further characterize these responses the inventors have isolated CD4 T cell clones specific for UCP2 and UCP4 from cancer patient. All the UCP4-specific CD4 T cell clones were strongly reactive in presence of cognate peptide, and showed a half-maximal TNF secretion observed at very low peptide concentration (<0.1 µM) (FIG. 2A, B). Similar results have been obtained for UCP2 specific clones with a half-maximal TNF secretion observed at ~4 µM (FIG. 2C, D). In addition, the inventors have showed after peptide stimulation that the clones mainly produced IFN-γ and TNF-α but not IL-4 nor IL-17A in agreement with a Th1 polarization (FIG. 2E). The reactivity of these CD4 T cell clones are inhibited by HLA-DR blocking antibody indicating their HLA-DR restriction.

Thus, these results showed that high avidity UCP-specific CD4 T cell clones can be generated from cancer patients and were Th1 polarized. They also demonstrate that these UCPs are naturally processed and presented to CD4 T cell in the context of malignancies.

Presence of Naturally Occurring CD4 T Cells Against UCPs in NSCLC Patients

Telomerase gene polymorphisms have been associated with lung cancer susceptibility and TERT expression is found in all types of NSCLC (Non small Lung Carcinoma) (Lantuejoul et al, Rafnar et al). Therefore the inventors have performed a comprehensive analysis of spontaneous UCP-specific CD4 T cell responses in a NSCLC. Ficoll-isolated blood lymphocytes from eighty-four advanced NSCLC patients have been collected prior first line chemotherapy and cultured shortly (one week) with the pool of UCPs and the specific T cells have been measured by IFN-γ. ELISPOT. Blood lymphocytes from 22 healthy volunteers have been used as control. Responses have been considered positive when the number of INF-γ secreting cells was at least two-fold above the negative control. This experimental design enables the inventors to measure specific CD4 T cell memory responses. As shown in FIG. 3A, UCP-specific memory immune responses has been found in 32 out of 84 patients (38%) whereas no specific IFN-γ responses against UCPs have been detected in healthy individuals. Analysis of the cytokine secretion profile of these responses reveals high production of TNF-α and IFN-γ in absence of IL-4, IL-17 and IL-10 indicating a Th1 polarization (data not shown). Analyzed individually, each of the four UCPs is able to generate a CD4 T cell response in patients. However, the frequency of T cell responses to UCP-2 and UCP-4 suggest that these peptides are more immunogenic (FIG. 3B). The absence of UCPs specific immune responses in patients could not be related to a global T cell anergy as illustrated by the presence of effective antiviral recall responses in patients without UCPs specific response (FIG. 3C). To exclude the influence of a number of immune parameters that have been reported to decrease antitumor response in NSCLC (Suzuki et al), the inventors have measured circulating CD4+ Foxp3+ regulatory T cells (Tregs) and the plasmatic IL-10 in the patients with or without UCP-specific immune response. The inventors have showed similar level of circulating Tregs in the two groups (FIG. 3D) and absence of plasmatic IL-10 detection by ELISA has been observed regardless the UCP-immune status (data not shown). In addition the total lymphocyte counts and neutrophil-lymphocyte ratio (NLR) are quite similar in these two groups (FIG. 3D).

The results indicate that patients with NSCLC are able to spontaneously mount TAA-specific CD4 T cell responses and that UCPs are prototypic peptides to monitor antitumor immune response in NSCLC.

Spontaneous UCP-Specific T Cell Immune Response Increase Overall Survival of Patients Responding to Chemotherapy The impact of the UCP-specific CD4 immune response on clinical outcome was analyzed in patients that responded or progressed after first line chemotherapy (CT). For this purpose, the inventors have focused on 55 out of 84 advanced NSCLC patients with a median follow-up of ten months.

All the patients included have been classified as metastatic stage IV. T-cell responses against TERT were not correlated with clinical or prognostic variables such as age, tobacco, ECOG PS status or histological subtype. Except six patients who received Erlotinib therapy, all patients were treated with platinum doublet. After first line, control disease (CD) based on RECIST criteria have been achieved in 36 out of 55 (65%), 25% of them achieved a partial response (PR) (14 out of 55) and 40% a stable disease (SD) (22 out of 55). Progressive disease (PD) has been observed in 19 out of 55 (35%). The frequency of spontaneous TERT-specific CD4 immune response was similar in patient with CD or PD after CT (FIG. 4A). In contrast patients displaying a TERT-specific immunity prior CT had an increased overall survival (OS) in the CD group compared to patients with no TERT-specific immunity (Median OS: 53 vs 40 weeks, p=0.034, HR=0.54, 95% CI [0.3-1]). The preexistence of UCP-specific immune response non-significantly increased the progression free survival (PFS) of CD patients (Median PFS: 33 vs 24 weeks, p=0.391, HR=0.76, 95% CI [0.4-0.7]) (FIG. 4B). Similar results have been observed when the inventors focused on patients that received platinum-based CT, after excluding the Erlotinib-treated patients (Median OS: 53 vs 40 weeks, p=0.049, HR=0.52 95% CI [0.3-0.9]) (FIG. 4C, D). By contrast, in patients with PD after first line CT, the inventors have found no survival difference regardless UCP-specific immune status (data not shown). Thus, the presence of natural TERT-specific CD4 Th1 responses in patients whose tumors are sensitive to chemotherapy is correlated to a higher OS.

Example 2

The Potent CD4 Helper Activity of Novel UCPs Derived from Telomerase on Self Antitumor CD8 T Cell Responses 2.1. Materials and Methods
Synthetic Peptides.

The four peptides derived from TERT called universal cancer peptides (UCPs): UCP1 (TERT44-58: PAAFRALVAQCLVCV, SEQ ID NO:4), UCP2 (TERT578-592: KSVWSKLQSIGIRQH, SEQ ID NO: 1), UCP3 (TERT916-930: GTAFVQMPAHGLFPW, SEQ ID NO:2) and UCP4 (TERT1041-1055: SLCYSILKAKNAGMS, SEQ ID NO:3) and the HLA-A2-restricted pY988 (YLQVNSLQTV, SEQ ID NO: 5) and pY572 (YLFFYRKSV, SEQ ID NO: 6) peptides derived from TERT have been used by the inventors. The native forms of the two cryptic HLA-A2 TERT peptides are fully conserved in human and mouse TERT (Hernandez et al, 2002). Synthetic peptides (>80% purity) were purchased from Activotec (UK).
Mouse.

The HLA-DRB1*0101/HLA-A*0201-transgenic mice (A2/DR1 mice) have been previously described (Pajot et al, 2004). These mice are H-2 class I and IA class II knockout and their CD8 T and CD4 T cells are restricted by the sole HLA-A*0201 and HLA-DR1*0101 molecules respectively.

Immunizations.

To study the processing of UCP, A2/DR1 mice were immunized with a pTrip-TERT DNA (100 µg) at days 0 and 14 as previously reported (Adotevi et al, 2010). In some experiment CD4 T cells were depleted with anti-CD4 mAb treatment (clone GK1.5) prior DNA immunization. For UCP immunization, mice were injected with 100 µg of each UCP emulsified in incomplete Freund adjuvant (IFA, Sigma-Aldrich, France). In some experiments, 50 µg of pY988 peptide was co-injected with 100 µg of each UCP in IFA. All peptide vaccinations were done subcutaneously (s.c) at the right abdominal flank. Eight to ten week-old mice were bred and maintained in our animal facilities. All experiments were done according to the good laboratory practices defined by animal experimentation rules in France.
Mouse Proliferation Assay.

Proliferation assays were performed ten days after the last DNA immunization as previously described (Pajot et al, 2004). Results are given as stimulation index=(cpm with specific peptide)/(cpm with irrelevant peptide).
Pentamer Staining and ELISPOT Assays.

Ex vivo pentamer staining was performed as previously described (Adotevi et al, 2010; Adotevi et al, 2006). Cells were stained with PE-conjugated pY988 and pY572 HLA-A2.1 pentamer (Prolmmune, UK). After cell staining, samples were analyzed by flow cytometry on a FACS Canto II (BD Biosciences, France) and using Diva software. Ex vivo ELISPOT was performed as previously described and following manufacturers instructions (GenProbe, France) (Adotevi et al, 2010; Adotevi et al, 2006)
Dendritic Cells Activation.

Spleen or lymph nodes CD11c+ DCs from peptide-immunized mice were directly analyzed for co-stimulatory receptor expression. In some experiments, immature bone marrow-derived DCs (iDC) from A2/DR1 mice were cultured 15-h with CD4 T cells from mice immunized with UCP or IFA alone and then stained for cell surface expression of co-stimulatory receptors and cytokines production.
Tumor Challenge.

The HLA-A2.1-positive B16F10 murine tumor cell line (referred as B16-A2) was previously shown to express high amounts of TERT (Adotevi et al, 2010). A2/DR1 mice were s.c. injected with 2.105 B16-A2 cells in 100 µl of saline buffer on the abdominal flank. At day 5, groups of mice were immunized with either the mix of pY988 and pY572 peptides (100 µg) with or without UCP2 (100 µg). A boost injection was done at day 17. Control mice were treated with adjuvant IFA in saline buffer. Tumor growth was monitored every 2-3 days using a calliper and mice were euthanized when the tumor mass reached a surface>200 mm2. The mice survival was assessed using the Kaplan-Meier model.
Detection of UCP-Specific T Cell Responses in Cancer Patients.

Blood was collected from cancer patients at the university hospital of Besancon (France) after informed consent. The study was conducted in accordance with French laws and after approval by the local ethics committee. Ficoll-isolated lymphocytes were analyzed by 3H thymidine incorporation as previously described (Pajot et al, 2004). After a short in vitro stimulation of lymphocytes with UCPs, UCP-specific immune response was analyzed by human ELISPOT assay (GenProbe). Concomitantly, cytokines production were measured after a 15H-culture with or without UCPs, using DIAplex Human Th1/Th2 kit (GenProbe) according to the manufacturers instructions, Statistics.

Data are presented as means±SD. Statistical comparison between groups was based on Student t test using Prism 4 GraphPad Software. Mouse survival time was estimated using the Kaplan-Meier method, and the log-rank test was used. P values less than 0.05 (*) were considered significant.

2.2. Results

Immunization with UCP Induces High Avidity Th1 Polarized CD4 T Cell Responses In Vivo The inventors and others have previously reported that the use of humanized HLA transgenic mice models to screen for human tumor antigens represents a potent alternative to optimize "reverse immunology" approaches for epitope identification (Adotevi et al, 2006; Osen et al, 2010). Here the inventors have used A2/DR1 mice to study the in vivo immunogenicity of UCPs, based on to their binding capacity to HLA-DRB1*0101 molecules. To assess whether UCPs can be endogenously processed from the TERT protein, the inventors performed immunizations with a plasmid DNA encoding the full length TERT sequence and the UCP-specific CD4 splenocytes were monitored by a five-day 3H-thymidine incorporation assay. As shown in FIG. 5A, all the UCPs differentially stimulate proliferation of spleen lymphocytes from DNA-immunized mice. Especially, high T cell proliferation was measured in response to UCP2 and 3 as compared to UCP1 or UCP4. The inventors have confirmed these results by using ex vivo IFN-γ ELISPOT assay and found strong UCP-specific CD4 T cell responses (FIG. 5B). Contrary to UCP1, specific CD4 T cell responses were detected against UCP2, 3 and 4 in all immunized mice (FIG. 5B). These data clearly indicate that UCPs are efficiently processed and presented to CD4 T cells in vivo in the context of DRB1*0101 restriction. Different populations of CD4 helper T cells control the antitumor immune responses (Pardoll et al, 1998), thus the inventors have studied the polarization of the UCP-specific CD4 T cell responses in vivo. To this end, freshly isolated CD4 T cells from UCP-vaccinated mice were cultured in the presence of syngenic iDC pulsed or not with UCP and cytokines production was measured. In all cases, the inventors have showed that UCP-specific CD4 T cells produce high level of IFN-γ and IL-2 but not IL-4, IL-5, IL-10 nor IL-17 indicating that UCP immunization preferentially induces a Th1 polarized immune response in vivo (FIG. 5C).

Next, to assess the avidity of UCP-specific CD4 T cell, freshly purified CD4 T cells from UCP-immunized mice were cultured in the presence of increasing concentrations of peptide and the number of specific IFN-γ producing CD4 T cells was measured by ELISPOT. Results in FIG. 5D showed that mice immunized with UCP2, UCP3 and UCP4 induced high avidity specific CD4 T cells ($<10^{-7}$ µM). By comparison CD4 T cells from mice vaccinated with UCP1 or UCP4 responded to $10^{-1}$ and $10^{-3}$ µM of peptide concentration respectively. Based on this, the inventors have concluded that low doses of UCP2 or UCP3 peptides (~1 µg) stimulated potent IFN-γ+ CD4 T cells in vivo (FIG. 5E). Collectively, UCPs are efficiently processed in vivo and stimulate high avidity Th1 polarized CD4 T cells in A2/DR1 mice.

UCP-Specific CD4 T Cells Provide Help for Optimal Anti-Self/TERT CD8 T Cell Responses In Vivo CD4 T cell helper functions are thought to be important for the generation of potent and sustained CTL responses (Shedlock et al, 2003). To address this question concerning UCP-specific CD4 T cells, the inventors co-immunized mice with self/TERT peptide pY988 in the presence of UCP. This peptide is fully conserved in human and mouse TERT sequences. The pY988-specific CTL response was measured ex vivo by pentamer staining and ELISPOT assays. As shown in FIG. 6A, a higher frequency of functional pY988-specific CD8 T cells was detected in mice immunized with pY988 plus UCP compared to mice vaccinated with pY988 alone. Although UCP1 vaccination had little impact on the frequency of pY988/A2 pentamer+ CD8 T cells-specific response, the four UCPs were able to significantly increase the number of IFN-γ-secreting CD8 T cells against self/TERT peptide (FIG. 6B). The magnitude of the pY988-specific CD8 T cells response was strongly correlated with the intensity of UCP-specific immune responses concomitantly induced in mice (FIGS. 6C, D). Furthermore, these UCPs exerted similar helper effect on the self/TERT pY572-specific CTL responses in vivo. Thus, the addition of UCPs as helper peptides efficiently breaks immune tolerance against self/TERT CD8 epitopes in vivo.

The inventors next have sought out to study the impact of UCPs helper peptides on CTL avidity and memory, two critical functions for tumor eradication. To this end the inventors focused on the UCP2 which induces potent Th1 immune responses in vivo. As shown in FIG. 7A, freshly isolated CD8 T cells from mice immunized with pY988+UCP2 were still reactive against very low concentrations of peptide pY988 ($<10^{-3}$ µM). These cells also recognized the cryptic native counterpart p988, underlining their high avidity (data not shown). Accordingly, mice vaccinated with pY988+UCP2 displayed stronger in vivo cytotoxicity against CFSE-labelled target cells than pY988 group (FIG. 7B). Thus, UCP2 helper immune responses enhance the quality of CTL response in vivo. This result supports a previous report showing that the stimulation of high avidity CD4+ T cells increases antitumor CTL avidity and cytolytic activity (Bandmaier et al, 2009). Furthermore, sustained anti-self/TERT CTL responses were detected in mice co-injected with UCP2 (FIG. 7C). This response was correlated to the long-lasting UCP2-specific CD4 T cell response in vivo (FIG. 7D). To confirm the role of UCP-specific CD4 T cell help, the inventors have showed that anti-self/TERT CD8 T cell response was strongly reduced in mice depleted of CD4 T cells prior to the TERT-DNA immunization as compared to non depleted mice (FIG. 7E). Similar results were obtained in other antigens model using peptides from HPV-16 E7 and NA-17 (data not shown). Thus, simultaneous stimulation of UCP-specific CD4 T cells is required for the optimal priming of tumor specific CTL in vivo.

UCP-Specific CD4 T Cells Promote Dendritic Cell Activation In Vivo

The induction of dendritic cell activation represents one major helper mechanism used by CD4+ Th1 cells to sustain antigen presentation and provide costimulatory signals to the CTLs. This is referred as the "ménage à trois" model (Ridge et al, 1998). To test this mechanism, the inventors have analyzed the expression of co-stimulating receptors on DCs from mice immunized with the mix of pY988+/−UCP2. As shown in FIG. 8A, lymph nodes CD11c+ DCs from UCP2/pY988 immunized mice expressed higher level of CD86, CD80, as well as HLA-class II molecules as compared to pY988-immunized mice. In a second set of experiments, isolated CD4 T cells from UCP2/IFA or IFA injected mice were co-cultured with syngenic iDCs as shown in FIG. 8B. As expected, UCP2-specific CD4 T cells produced significant amounts of Th1 cytokines such as IFN-γ and GM-CSF (FIG. 8C). The inventors have shown that the presence of UCP2-specific CD4 T cells induced potent DCs activation and enhanced their ability to produce high amounts of interleukin-12 (FIGS. 8D, E). Together, these results showed that the stimulation of UCP2-specific T cells shapes the phenotype and function of DCs in vivo.

UCP2 Helper Peptide Enhances the Efficacy of Self/TERT CD8 Peptides Vaccination Against Established 816-A2 Melanoma To investigate the helper role of UCP in a therapeutic vaccination protocol, the inventors have focused on the UCP2 helper peptide which exhibits potent CTL helper function in vivo. The aggressive and poor immunogenic B16F10-HLA-A*0201 melanoma model was used in A2/DR1 mice. As previously reported this cell line highly expresses functional murine TERT (FIG. 9A) and is recognized by the self/TERT-specific CTLs (Adotevi et al, 2010). Tumor bearing mice were vaccinated twice either with two self/TERT CTL peptides (pY572+pY988/IFA) alone or in presence of the UCP2 helper peptide. As shown in FIG. 9B, the tumor growth reached an area >200 mm² at day 25 in the control group injected with the adjuvant IFA alone. In this representative experiment, tumor regression was observed in 1/8 mice vaccinated with pY572+pY988/IFA while two mice achieved a delay in tumor growth. In the group vaccinated with pY988+pY572/IFA combined with UCP2, complete tumor regression was achieved in 5/8 mice. Accordingly, survival analysis out to day 50 after tumor cell injection showed that 63% of mice vaccinated in presence of UCP2 were still alive as compared to 13% in the group of mice injected with pY988+pY572/IFA (p<0.05) (FIG. 9C). Two months later, anti-pY988 effector CTL response was detected in tumor free mice and this was correlated to long term UCP2-specific CD4 T cell response in vivo (FIG. 9D). This sustained T cell immunity provides protection against a second lethal dose of B16/A2 tumors.

The density of tumor-infiltrating CD8 T cells was shown to be critical for tumor control (Galon et al, 2006). Therefore, the inventors have analyzed immune cell infiltration within tumor in mice treated with the same vaccination protocols. Higher total CD3+ CD8+ T cells infiltration was observed in mice that received vaccine plus UCP2 helper peptide as compared to pY988+pY572/IFA group (67% vs 40%, p<0.05) (FIG. 9E). In contrast, UCP vaccination did not influence NK cells or regulatory T cells tumor infiltration (FIG. 9E), suggesting that UCP2-specific immune response mainly drive effector CTLs at the tumor microenvironment.

Together, our results clearly showed that UCP2 specific CD4 T cells exert strong helper activity on tumor-specific CTL responses in vivo. Moreover the addition of UCP2 influences the homing of CD8 T cells to the tumor site. All these data support the use of UCP for antitumor therapeutic vaccination.

Naturally Occurring UCP-Specific CD4 T Cell Responses in Human Cancers

Based on the broad expression of TERT in cancers, the inventors have sought for UCP-specific CD4 T cell responses in patients with cancer of different histological origins. For this purpose, the inventors have measured 3H-thymidine incorporation of blood lymphocytes obtained from cancer patients directly stimulated with UCPs during 6 days. As shown in FIG. 10A, specific T cell proliferation was induced upon UCP stimulation. Next, UCP-specific T cells were measured by IFN-γ ELISPOT after short-term in vitro stimulation of PBMCs. The inventors have found high numbers of IFN-γ-producing T cells directed against UCP in various cancers such as colon, renal, lung, stomach, and leukaemia supporting the T cell proliferation response (FIG. 10B). The UCP-specific T cells mainly produce Th1 cytokines but no IL-4, IL-10 or IL-17 in agreement with the in vivo studies of the inventors (FIG. 10C). As previously shown, T cell responses against individual UCP were also found in the PBMCs of patients presenting various cancers, supporting the idea that UCP epitopes are promiscuous (FIG. 10D). To study more precisely the polarization of UCP-specific CD4 T cells, the inventors have generated CD4 T cell clones specific for UCP4 derived from one responding colorectal cancer patient (FIG. 11A). Compared to CD4 T cells from healthy donors, these clones expressed a two-fold increased level of T-bet mRNA and lower GATA-3, RORγc, and Foxp3 mRNA expressions (FIG. 11B). In addition these clones produced high amounts of IFN-γ, TNF-α and a few IL-10, but no IL-13 nor IL-17, a cytokine pattern related to Th1 (FIG. 11C). Thus, these results indicate that the UCP-specific T cell repertoire is spontaneously stimulated in cancer patients and that these UCP-specific immune responses are Th1 polarized.

REFERENCES

Adotevi O, Mollier K, Neuveut C, et al. Immunogenic HLA-B*0702-restricted epitopes derived from human telomerase reverse transcriptase that elicit antitumor cytotoxic T-cell responses. Clin Cancer Res 2006; 12:3158-67.

Adotevi O, Mollier K, Neuveut C, et al. Targeting human telomerase reverse transcriptase with recombinant lentivector is highly effective to stimulate antitumor CD8 T-cell immunity in vivo. Blood 2010; 115:3025-32.

Artandi S E, DePinho R A. Telomeres and telomerase in cancer. Carcinogenesis; 31:9-18. Bevan M J. Helping the CD8(+) T-cell response. Nat Rev Immunol 2004; 4:595-602.

Bennett S R, Carbone F R, Karamalis F, Flavell R A, Miller J F, Heath W R. Help for cytotoxic-T-cell responses is mediated by CD40 signalling. Nature 1998; 393: 478-80.

Boni A, Cogdill A P, Dang P, et al. Selective BRAFV600E inhibition enhances T-cell recognition of melanoma without affecting lymphocyte function. Cancer Res; 70:5213-9.

Bos R, Sherman L A. CD4+ T-cell help in the tumor milieu is required for recruitment and cytolytic function of CD8+ T lymphocytes. Cancer Res; 70:8368-77.

Brandmaier A G, Leitner W W, Ha S P, Sidney J, Restifo N P, Touloukian C E. High-avidity autoreactive CD4+ T cells induce host CTL, overcome T(regs) and mediate tumor destruction. J Immunother 2009; 32:677-88.

Brunsvig P F, Kyte J A, Kersten C, et al. Telomerase Peptide Vaccination in NSCLC: A Phase II Trial in Stage III Patients Vaccinated after Chemoradiotherapy and an 8-Year Update on a Phase I/II Trial. Clin Cancer Res; 17:6847-57.

Campi G, Crosti M, Consogno G, et al. CD4(+) T cells from healthy subjects and colon cancer patients recognize a carcinoembryonic antigen-specific immunodominant epitope. Cancer Res 2003; 63:8481-6.

Fridman W H, Galon J, Pages F, Tartour E, Sautes-Fridman C, Kroemer G. Prognostic and predictive impact of intra- and peritumoral immune infiltrates. Cancer Res; 71:5601-5.

Galon J, Costes A, Sanchez-Cabo F, et al. Type, density, and location of immune cells within human colorectal tumors predict clinical outcome. Science 2006; 313:1960-4.

Godet Y, Desfrancois J, Vignard V, et al. Frequent occurrence of high affinity T cells against MELOE-1 makes this antigen an attractive target for melanoma immunotherapy. Eur J Immunol; 40:1786-94.

Hanahan D, Weinberg R A. Hallmarks of cancer: the next generation. Cell; 144:646-74.

Hernandez J, Garcia-Pons F, Lone Y C, et al. Identification of a human telomerase reverse transcriptase peptide of low affinity for HLA A2.1 that induces cytotoxic T lymphocytes and mediates lysis of tumor cells. Proc Natl Acad Sci USA 2002; 99:12275-80.

Kantoff P W, Higano C S, Shore N D, et al. Sipuleucel-T immunotherapy for castration-resistant prostate cancer. N Engl J Med; 363:411-22.

Kennedy R, Celis E. Multiple roles for CD4+ T cells in anti-tumor immune responses. Immunol Rev 2008; 222:129-44.

Kobayashi H, Celis E. Peptide epitope identification for tumor-reactive CD4 T cells. Curr Opin Immunol 2008; 20:221-7.

Kobayashi H, Wood M, Song Y, Appella E, Celis E. Defining promiscuous MHC class II helper T-cell epitopes for the HER2/neu tumor antigen. Cancer Res 2000; 60:5228-36.

Kono M, Dunn I S, Durda P J, et al. Role of the mitogen-activated protein kinase signaling pathway in the regulation of human melanocytic antigen expression. Mol Cancer Res 2006; 4:779-92.

Kyte J A, Gaudernack G, Dueland S, Trachsel S, Julsrud L, Aamdal S. Telomerase peptide vaccination combined with temozolomide: a clinical trial in stage IV melanoma patients. Clin Cancer Res 2011; 17:4568-80.

Lantuejoul S, Salon C, Soria J C, Brambilla E. Telomerase expression in lung preneoplasia and neoplasia. Int J Cancer 2007; 120:1835-41.

Martinez P, Blasco M A. Telomeric and extra-telomeric roles for telomerase and the telomere-binding proteins. Nat Rev Cancer; 11:161-76.

Nakanishi Y, Lu B, Gerard C, Iwasaki A. CD8(+) T lymphocyte mobilization to virus-infected tissue requires CD4(+) T-cell help. Nature 2009; 462:510-3.

Osen W, Soltek S, Song M, et al. Screening of human tumor antigens for CD4 T cell epitopes by combination of HLA-transgenic mice, recombinant adenovirus and antigen peptide libraries. PLoS One 2010; 5: e14137.

Pajot A, Michel M L, Fazilleau N, et al. A mouse model of human adaptive immune functions: HLA-A2.1-/HLA-DR1-transgenic H-2 class I-/class II-knockout mice. Eur J Immunol 2004; 34:3060-9.

Pardoll D M, Topalian S L. The role of CD4+ T cell responses in antitumor immunity. Curr Opin Immunol 1998; 10:588-94.

Perez-Diez A, Joncker N T, Choi K, et al. CD4 cells can be more efficient at tumor rejection than CD8 cells. Blood 2007; 109:5346-54.

Rafnar T, Sulem P, Stacey S N, et al. Sequence variants at the TERT-CLPTM1L locus associate with many cancer types. Nat Genet 2009; 41:221-7.

Rakhra K, Bachireddy P, Zabuawala T, et al. CD4(+) T cells contribute to the remodeling of the microenvironment required for sustained tumor regression upon oncogene inactivation. Cancer Cell; 18:485-98.

Ridge J P, Di Rosa F, Matzinger P. A conditioned dendritic cell can be a temporal bridge between a CD4+ T-helper and a T-killer cell. Nature 1998; 393:474-8.

Robert C, Thomas L, Bondarenko I, et al. Ipilimumab plus dacarbazine for previously untreated metastatic melanoma. N Engl J Med; 364:2517-26.

Scardino A, Gross D A, Alves P, et al. HER-2/neu and hTERT cryptic epitopes as novel targets for broad spectrum tumor immunotherapy. J Immunol 2002; 168:5900-6.

Schlapbach C, Yerly D, Daubner B, Yawalkar N, Hunger R E. Telomerase-specific GV1001 peptide vaccination fails to induce objective tumor response in patients with cutaneous T cell lymphoma. J Dermatol Sci 2011; 62:75-83.

Schroers R, Huang X F, Hammer J, Zhang J, Chen S Y. Identification of HLA DR7-restricted epitopes from human telomerase reverse transcriptase recognized by CD4+ T-helper cells. Cancer Res 2002; 62:2600-5.

Schroers R, Shen L, Rollins L, et al. Human telomerase reverse transcriptase-specific T-helper responses induced by promiscuous major histocompatibility complex class II-restricted epitopes. Clin Cancer Res 2003; 9:4743-55.

Shedlock D J, Shen H. Requirement for CD4 T cell help in generating functional CD8 T cell memory. Science 2003; 300:337-9.

Smith C M, Wilson N S, Waithman J, et al. Cognate CD4(+) T cell licensing of dendritic cells in CD8(+) T cell immunity. Nat Immunol 2004; 5:1143-8.

Street S E, Cretney E, Smyth M J. Perforin and interferon-gamma activities independently control tumor initiation, growth, and metastasis. Blood 2001; 97:192-7.

Suzuki K, Kachala S S, Kadota K, et al. Prognostic immune markers in non-small cell lung cancer. Clin Cancer Res; 17:5247-56.

Tosolini M, Kirilovsky A, Mlecnik B, et al. Clinical impact of different classes of infiltrating T cytotoxic and helper cells (Th1, th2, treg, th17) in patients with colorectal cancer. Cancer Res; 71:1263-71.

Wang X F, Kerzerho J, Adotevi O, et al. Comprehensive analysis of HLA-DR- and HLA-DP4-restricted CD4+ T cell response specific for the tumor-shared antigen survivin in healthy donors and cancer patients. J Immunol 2008; 181:431-9.

Zitvogel L, Kepp O, Kroemer G. Immune parameters affecting the efficacy of chemotherapeutic regimens. Nat Rev Clin Oncol; 8:151-60.

---

The invention claimed is:

1. A method for treating a tumor in a patient in need thereof, wherein the method comprises administering to the patient (i) a first peptide consisting of the sequence SLCYSILKAKNAGMS (SEQ ID NO: 3), and (ii) a second peptide consisting of the sequence KSVWSKLQSIGIRQH (SEQ ID NO: 1).

2. The method of claim 1, wherein the method further comprises administering to the patient (iii) a third peptide consisting of the sequence GTAFVQMPAHGLFPW (SEQ ID NO: 2) and (iv) a fourth peptide consisting of the sequence PAAFRALVAQCLVCV (SEQ ID NO: 4).

3. The method of claim 1, wherein the method further comprises administering an immunogenic tumor antigen.

4. The method of claim 1, wherein the tumor is a cancer.

5. The method of claim 4, wherein the cancer is selected from the group consisting of chronic lymphocytic leukemia, chronic myeloid leukemia, multiple myeloma, malignant myeloma, Hodgkin's disease, melanoma, brain cancer, carcinomas of the bladder, breast, cervix, colon, lung, pancreas, prostate, head and neck, and stomach.

6. The method of claim 4, wherein the cancer is a lung cancer.

7. The method of claim 2, wherein the tumor is a lung cancer and the method comprises administering peptides KSVWSKLQSIGIRQH (SEQ ID NO: 1), GTAFVQMPAHGLFPW (SEQ ID NO: 2), SLCYSILKAKNAGMS (SEQ ID NO: 3), and PAAFRALVAQCLVCV (SEQ ID NO: 4).

* * * * *

SEQUENCE LISTING

```
<160> NUMBER OF SEQ ID NOS: 6

<210> SEQ ID NO 1
<211> LENGTH: 15
<212> TYPE: PRT
<213> ORGANISM: Homo sapiens

<400> SEQUENCE: 1

Lys Ser Val Trp Ser Lys Leu Gln Ser Ile Gly Ile Arg Gln His
1               5                   10                  15
```

```
<210> SEQ ID NO 2
<211> LENGTH: 15
<212> TYPE: PRT
<213> ORGANISM: Homo sapiens

<400> SEQUENCE: 2

Gly Thr Ala Phe Val Gln Met Pro Ala His Gly Leu Phe Pro Trp
1               5                   10                  15

<210> SEQ ID NO 3
<211> LENGTH: 15
<212> TYPE: PRT
<213> ORGANISM: Homo sapiens

<400> SEQUENCE: 3

Ser Leu Cys Tyr Ser Ile Leu Lys Ala Lys Asn Ala Gly Met Ser
1               5                   10                  15

<210> SEQ ID NO 4
<211> LENGTH: 15
<212> TYPE: PRT
<213> ORGANISM: Homo sapiens

<400> SEQUENCE: 4

Pro Ala Ala Phe Arg Ala Leu Val Ala Gln Cys Leu Val Cys Val
1               5                   10                  15

<210> SEQ ID NO 5
<211> LENGTH: 10
<212> TYPE: PRT
<213> ORGANISM: Homo sapiens

<400> SEQUENCE: 5

Tyr Leu Gln Val Asn Ser Leu Gln Thr Val
1               5                   10

<210> SEQ ID NO 6
<211> LENGTH: 9
<212> TYPE: PRT
<213> ORGANISM: Homo sapiens

<400> SEQUENCE: 6

Tyr Leu Phe Phe Tyr Arg Lys Ser Val
1               5
```